US011977259B2

(12) United States Patent
Hajati et al.

(10) Patent No.: US 11,977,259 B2
(45) Date of Patent: May 7, 2024

(54) OPTICAL TRANSCEIVER ARRAYS

(71) Applicant: LYTE AI, INC., Mountain View, CA (US)

(72) Inventors: Arman Hajati, San Carlos, CA (US); Yuval Gerson, Sunnyvale, CA (US); Alexander Shpunt, Saratoga, CA (US)

(73) Assignee: LYTE AI, INC., Mountain View, CA (US)

( * ) Notice: Subject to any disclaimer, the term of this patent is extended or adjusted under 35 U.S.C. 154(b) by 0 days.

(21) Appl. No.: 18/261,675

(22) PCT Filed: Aug. 17, 2022

(86) PCT No.: PCT/US2022/040527
§ 371 (c)(1),
(2) Date: Jul. 17, 2023

(87) PCT Pub. No.: WO2023/023106
PCT Pub. Date: Feb. 23, 2023

(65) Prior Publication Data
US 2024/0069285 A1 Feb. 29, 2024

Related U.S. Application Data

(60) Provisional application No. 63/342,176, filed on May 16, 2022, provisional application No. 63/240,012, (Continued)

(51) Int. Cl.
*G02B 6/28* (2006.01)
*G01S 7/481* (2006.01)
(Continued)

(52) U.S. Cl.
CPC .......... *G02B 6/2817* (2013.01); *G01S 7/4814* (2013.01); *G01S 7/4816* (2013.01);
(Continued)

(58) Field of Classification Search
None
See application file for complete search history.

(56) References Cited

U.S. PATENT DOCUMENTS 8,593,711 B2  11/2013 Borchers et al.
9,007,569 B2  4/2015 Amzajerdian et al.
(Continued)

FOREIGN PATENT DOCUMENTS

CN  111722237 A  9/2020
CN  113227823 A  8/2021
(Continued)

OTHER PUBLICATIONS

International Application # PCT/US23/67587 Search Report dated Sep. 7, 2023.
(Continued)

*Primary Examiner* — Jerry Rahll
(74) *Attorney, Agent, or Firm* — Kligler & Associates Patent Attorneys Ltd.

(57) ABSTRACT

An optoelectronic device (20, 50) includes a planar substrate (30), an optical bus (40, 82, 84, 96, 140, 150, 180, 182, 224) disposed on the substrate and configured to convey coherent radiation through the bus, and an array (32, 72) of sensing cells (34, 74, 90, 160, 170, 200, 212, 380) disposed on the substrate. Each sensing cell includes at least one tap (92, 94, 144, 146, 226, 228) coupled to extract a portion of the coherent radiation propagating through the optical bus, an optical transducer (36, 108, 162, 172, 202, 204, 214) configured to couple optical radiation between the sensing cell and a target external to the substrate, and a receiver (114, 174, 178, 216, 218), which is coupled to mix the coherent radiation extracted by the tap with the optical radiation received by the optical transducer and to output an electrical signal responsively to the mixed radiation.

46 Claims, 23 Drawing Sheets

Related U.S. Application Data filed on Sep. 2, 2021, provisional application No. 63/234,700, filed on Aug. 18, 2021.

(51) Int. Cl.

| | | |
|---|---|---|
| *G01S 17/34* | (2020.01) | |
| *G02B 6/02* | (2006.01) | |
| *G02B 6/12* | (2006.01) | |
| *G02B 6/35* | (2006.01) | |

(52) U.S. Cl.
CPC ............ *G01S 7/4817* (2013.01); *G01S 17/34* (2020.01); *G02B 6/0208* (2013.01); *G02B 6/3588* (2013.01); *G02B 2006/1215* (2013.01)

(56) References Cited

U.S. PATENT DOCUMENTS

| | | | |
|---|---|---|---|
| 9,683,928 | B2 | 6/2017 | Swanson |
| 2002/0030094 | A1 | 3/2002 | Curry et al. |
| 2008/0019693 | A1 | 1/2008 | Sorin |
| 2008/0167819 | A1 | 7/2008 | Breed |
| 2009/0310118 | A1 | 12/2009 | Halldorsson |
| 2014/0276108 | A1 | 9/2014 | Vertikov |
| 2017/0067829 | A1 | 3/2017 | Duer |
| 2017/0317750 | A1 | 11/2017 | Chaffee et al. |
| 2019/0004247 | A1 | 1/2019 | Huang et al. |
| 2020/0003975 | A1 | 1/2020 | Yu et al. |
| 2020/0076152 | A1 | 3/2020 | Eichenholz et al. |
| 2020/0124711 | A1 | 4/2020 | Rezk et al. |
| 2020/0169056 | A1 | 5/2020 | Popovic et al. |
| 2020/0174124 | A1 | 6/2020 | Raring et al. |
| 2020/0284883 | A1* | 9/2020 | Ferreira ............... G01S 7/4816 |
| 2020/0284981 | A1 | 9/2020 | Harris et al. |
| 2020/0301244 | A1 | 9/2020 | Wang |
| 2021/0055694 | A1 | 2/2021 | Chan et al. |
| 2021/0072384 | A1 | 3/2021 | Balbas |
| 2021/0373157 | A1 | 12/2021 | Pierrottet et al. |
| 2022/0011409 | A1 | 1/2022 | Hosseini et al. |
| 2022/0236384 | A1 | 7/2022 | Sutton et al. |

FOREIGN PATENT DOCUMENTS

| | | |
|---|---|---|
| JP | 6696782 B2 | 5/2020 |
| WO | 2021116766 A1 | 6/2021 |
| WO | 2023023105 A1 | 2/2023 |
| WO | 2023023106 A2 | 2/2023 |
| WO | 2023034465 A2 | 3/2023 |
| WO | 2023076132 A1 | 5/2023 |

OTHER PUBLICATIONS

International Appliction # PCT/US2022/40527 Search Report dated Feb. 3, 2023.

Xi et al., "Generic Real-time Uniform K-Space Sampling Method for High-speed Swept-source Optical Coherence Tomography," Optics Express, vol. 18, issue 9, pp. 1-7, Apr. 26, 2010.
International Application # PCT/US2022/040526 Search Report dated Jan. 18, 2023.
International Application # PCT/US2022/42281 Search Report dated Feb. 28, 2023.
International Application # PCT/US2022/47516 Search Report dated Mar. 6, 2023.
Dai et al., "Novel Concept for Ultracompact Polarization Splitter-rotator Based on Silicon Nanowires," Optics Express, vol. 19, No. 11, pp. 10940-10949, year 2011.
Guan et al., "CMOS-compatible Highly Efficient Polarization Splitter and Rotator Based on a Double-etched Directional Coupler," Optics Epress, vol. 22, No. 3, pp. 2489-2496, year 2014.
Bhandari et al., "Highly Efficient Broadband Silicon Nitride Polarization Beam Splitter Incorporating Serially Cascaded Asymmetric Directional Couplers," Optics Letters, vol. 45, No. 21, pp. 5974-5977, year 2020.
Guan et al., "Ultracompact Silicon-on-insulator Polarization Rotator for Polarization-diversified Circuits," Optics Letters, vol. 39, No. 16, pp. 4703-4706, year 2014.
Popov et al., "A Laser Speckle Pattern Technique for Designing an Optical Computer Mouse," Optics and Lasers in Engineering, vol. 42, pp. 21-26, year 2004.
Jo et al., "SpeDo: 6 DOF Ego-Motion Sensor Using Speckle Defocus Imaging," Columbia University, pp. 1-13, year 2015.
Gupta, "SpeDo: 6 DOF Ego-Motion Sensor Using Speckle Defocus Imaging," YouTube demonstration, pp. 1-2, year 2016, as downloaded from https://youtu.be/liiBMx40KLM.
Amzajerdian et al., "Navigation Doppler Lidar for Autonomous Ground, Aerial, and Space Vehicles," NASA, pp. 1-2, year 2018.
Synopsys, Inc., "Designing Mode MUX/DEMUX Structures for Spatial Division Multiplexing Systems," pp. 1-7, year 2021, as downloaded from https://www.synopsys.com/photonic-solutions/product-applications/communications/beamprop-mode-sdm.html.
Pierrottet et al, "Navigation Doppler Lidar Sensor for Precision Altitude and Vector Velocity Measurements Flight Test Results," NASA, pp. 1-11, year 2011, as downloaded from https://ntrs.nasa.gov/api/citations/20120003317/downloads/20120003317.pdf.
Amazajerdian et al., "Doppler Lidar Sensor for Precision Landing on the Moon and Mars," NASA, pp. 1-7, year 2012, as downloaded from https://ntrs.nasa.gov/api/citations/20120003334/downloads/20120003334.pdf.
Noriki et al., "45-degree Curved Micro-mirror for Vertical Optical I/O of Silicon Photonics Chip," Optics Express, vol. 27, issue 14, pp. 19749-19757, year 2019.
International Application # PCT/US23/66982 filed May 15, 2023.
International Application # PCT/US23/67587 filed May 28, 2023.
International Application # PCT/US2023/066982 Search Report Jan. 25, 2024.

* cited by examiner

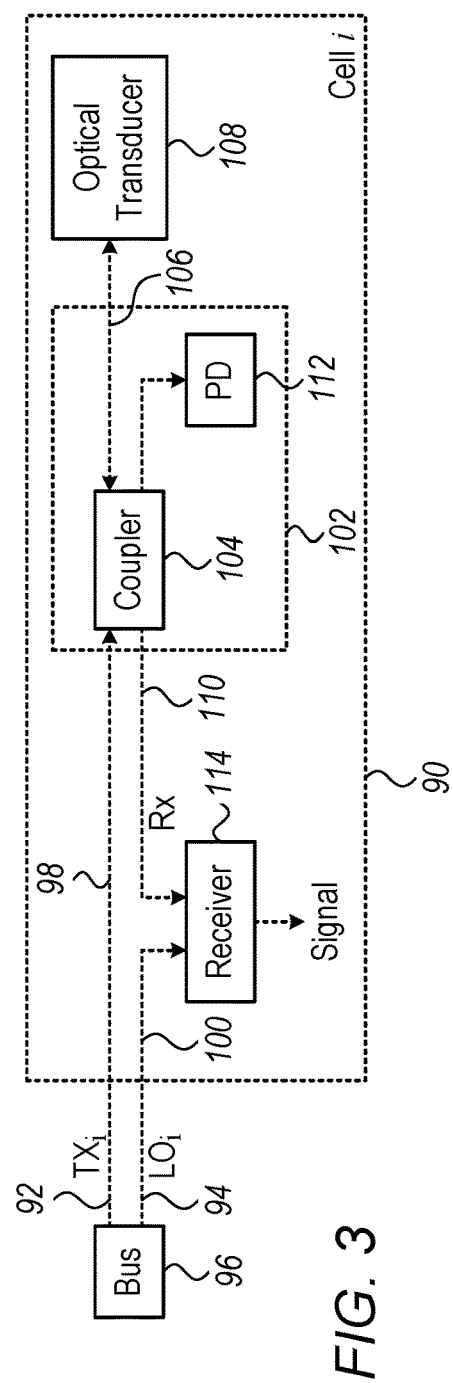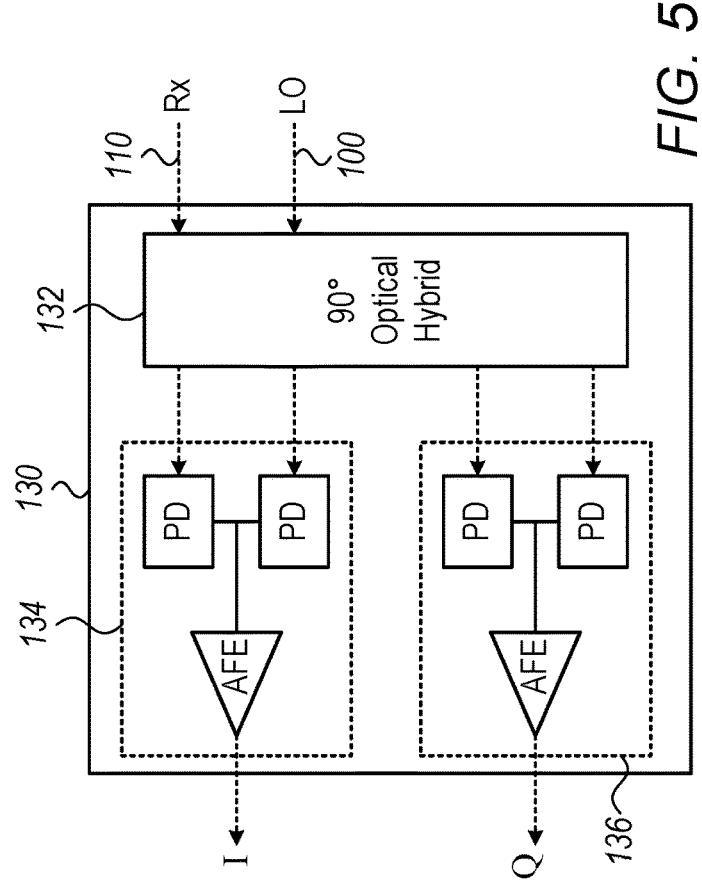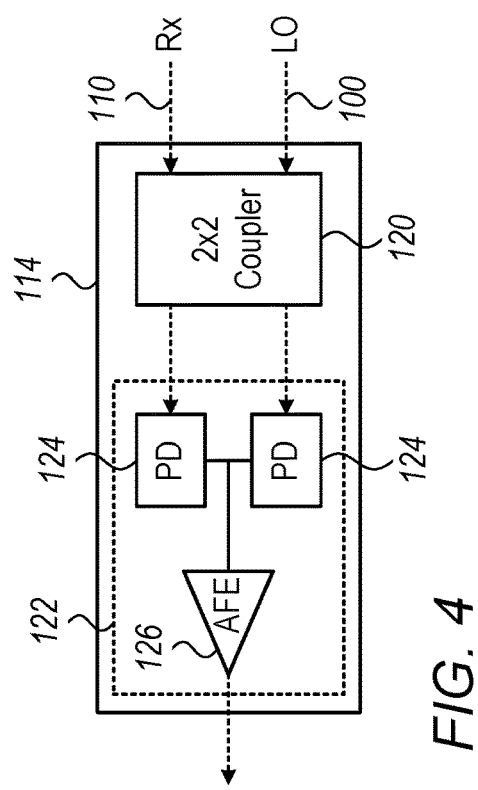
FIG. 3
FIG. 4
FIG. 5

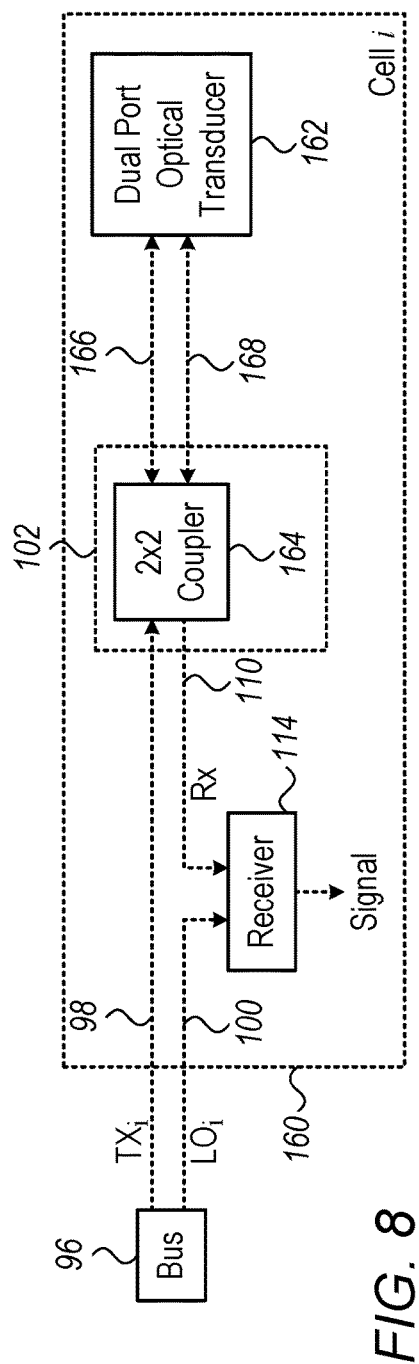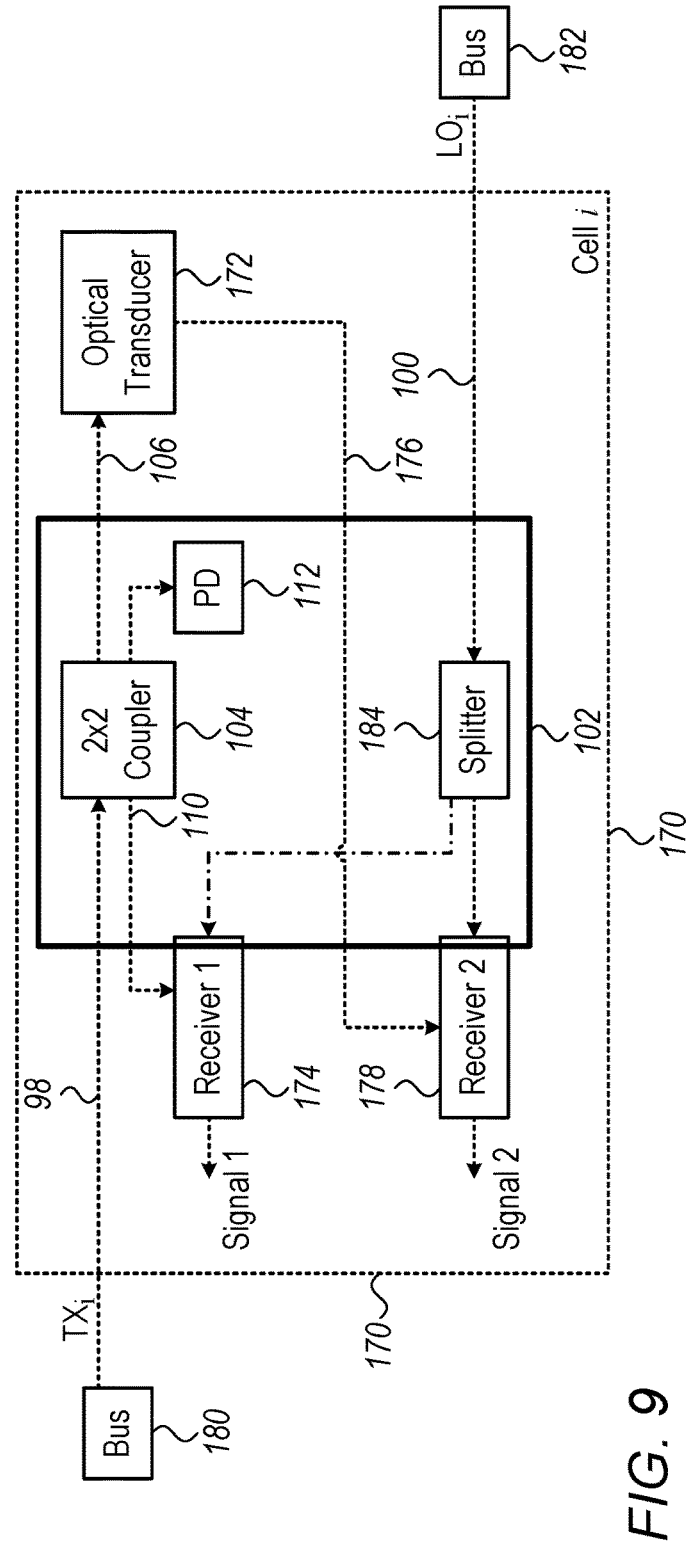
FIG. 8
FIG. 9

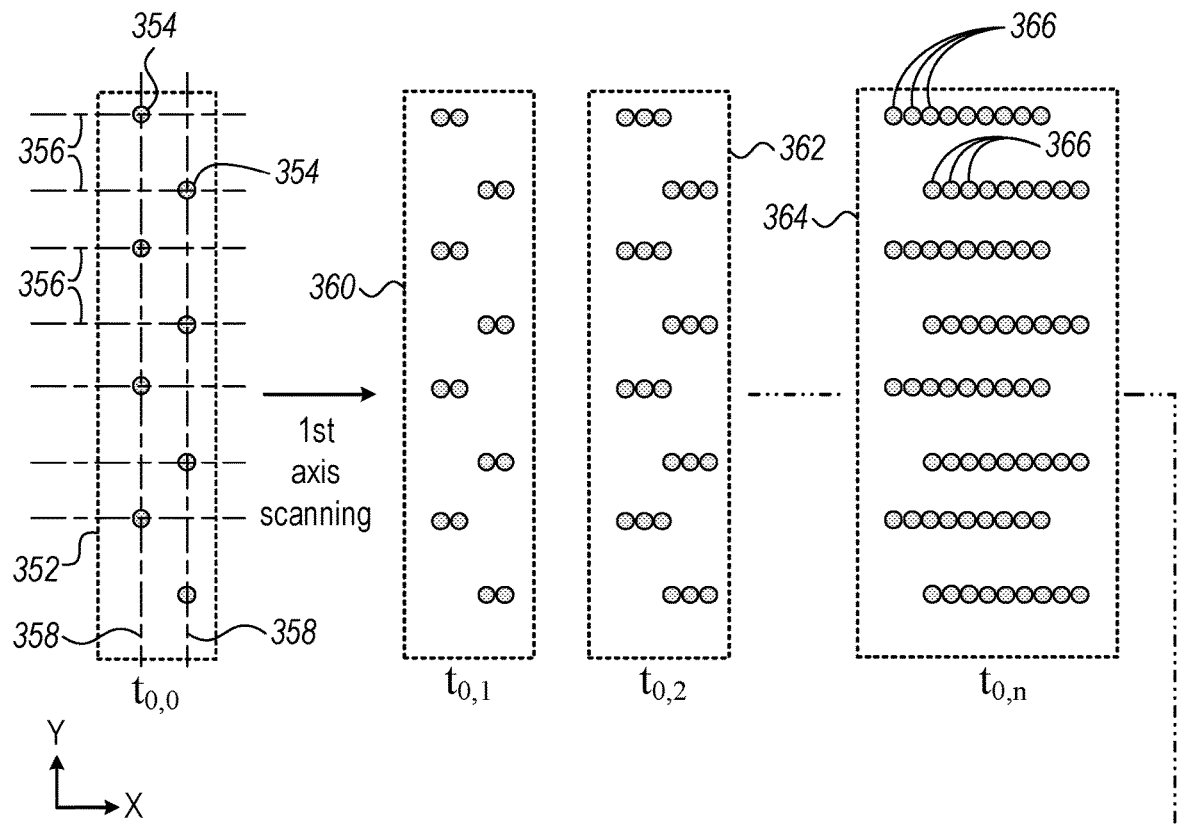
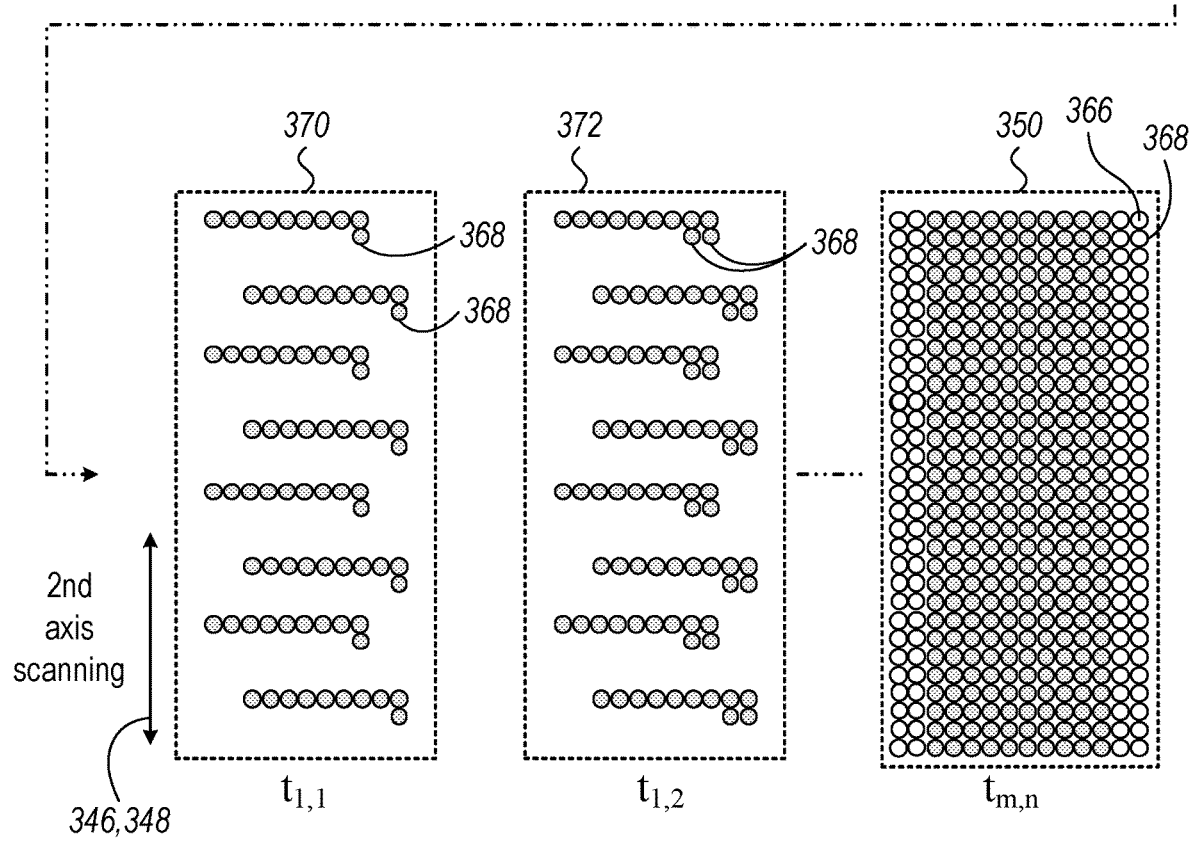
FIG. 21

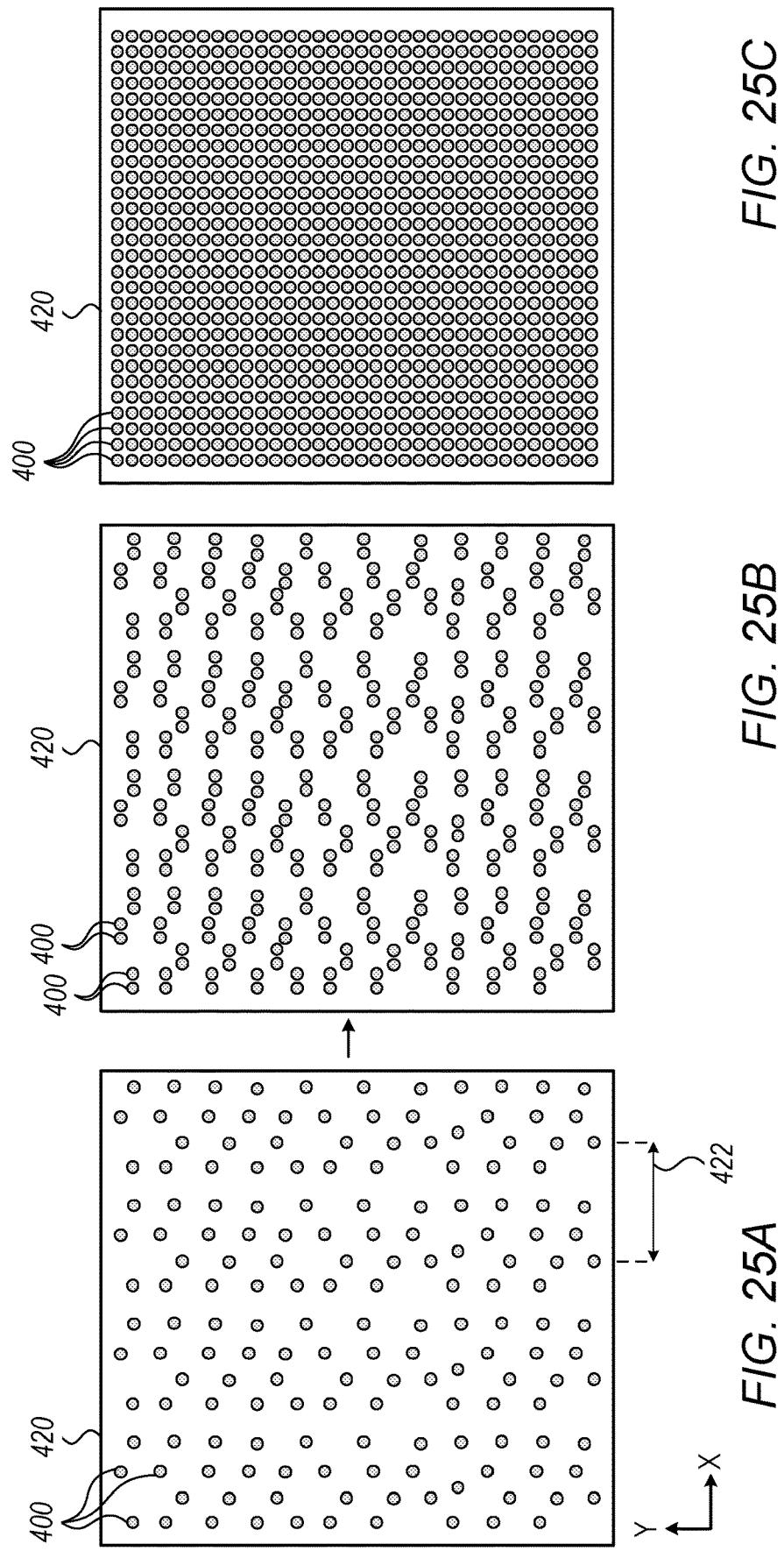

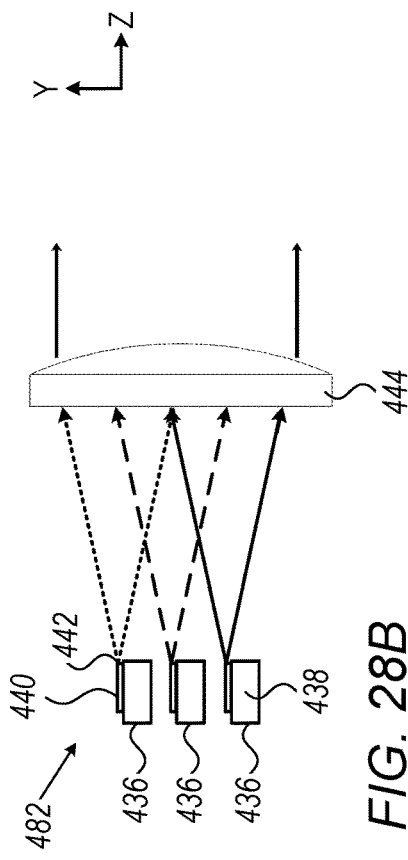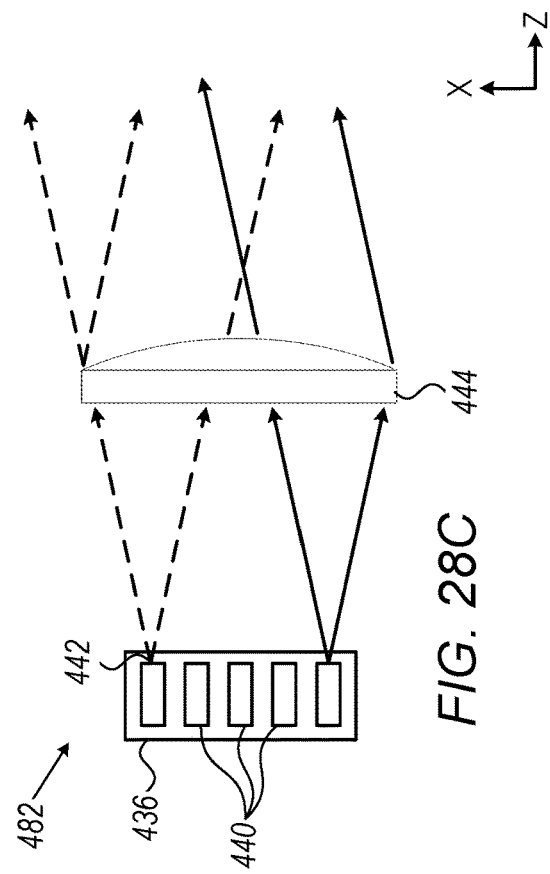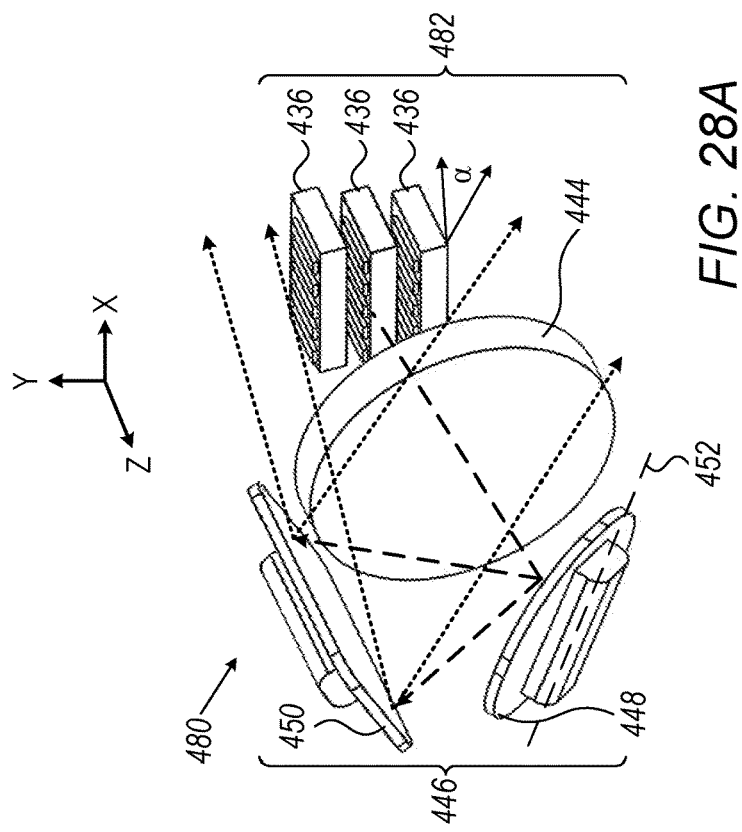

OPTICAL TRANSCEIVER ARRAYS

CROSS-REFERENCE TO RELATED APPLICATION

This application claims the benefit of U.S. Provisional Patent Application 63/234,700, filed Aug. 18, 2021; U.S. Provisional Patent Application 63/240,012, filed Sep. 2, 2021; and U.S. Provisional Patent Application 63/342,176, filed May 16, 2022. This application is related to another PCT patent application, filed on even date, entitled "Integrated arrays for coherent optical detection". The disclosures of all these related applications are incorporated herein by reference.

FIELD OF THE INVENTION

The present invention relates generally to systems and methods for optical sensing, and particularly to integrated optical sensing devices.

BACKGROUND

In many optical sensing applications, multiple points on a target are irradiated by an optical beam or beams, and the reflected radiation from each point is processed to analyze properties of the target. In some applications, such as optical coherence tomography (OCT) and continuous-wave (CW) LiDAR, a coherent beam is transmitted toward the target, and the reflected radiation is sensed and processed coherently with the transmitted radiation. To sense the properties of the target with high resolution, the transmitted beam may be scanned over the target area, or an array of multiple beams may be transmitted and sensed simultaneously using an array of receivers.

The terms "optical," "light," and "optical radiation," as used in the present description and in the claims, refer to electromagnetic radiation in any of the visible, infrared, and ultraviolet spectral ranges.

SUMMARY

Embodiments of the present invention that are described hereinbelow provide improve systems, devices, and methods for optical sensing.

There is therefore provided, in accordance with an embodiment of the invention, an optoelectronic device, including a planar substrate and an optical bus including at least one waveguide disposed on the substrate and configured to convey coherent radiation through the bus. An array of sensing cells is disposed on the substrate along the optical bus. Each sensing cell includes at least one tap coupled to extract a portion of the coherent radiation propagating through the optical bus, an optical transducer, configured to couple optical radiation between the sensing cell and a target external to the substrate, and a receiver, which is coupled to mix the coherent radiation extracted by the tap with the optical radiation received by the optical transducer and to output an electrical signal responsively to the mixed radiation.

In some embodiments, the optical bus includes multiple buses serving different, respective sets of the sensing cells, and the device includes an optical network coupled to distribute the coherent radiation from a radiation source to the multiple buses. In one embodiment, the optical network includes an active switch network. Alternatively or additionally, the optical network includes a passive splitter array.

In some embodiments, the sensing cells have respective fields of view, which are defined by respective optical apertures of the optical transducers, and the device includes a scanner, which is configured to scan the fields of view over the target. In a disclosed embodiment, the optical apertures are disposed in a row, which has a row axis perpendicular to a scan direction of the scanner. Additionally or alternatively, the optical apertures of the sensing cells are located at respective nodes on respective rows and columns of a two-dimensional rectangular grid such that only a minority of the nodes on the respective rows and columns are occupied by the optical transducers, and the scanner is configured to scan the optical apertures across the target along at least the rows of the grid so that each of the optical apertures is projected successively onto a respective sequence of multiple nodes in the rectangular grid on the target.

In some embodiments, each sensing cell includes a transmit waveguide, which is configured to convey the coherent radiation from the at least one tap to the optical transducer for transmission toward the target, and a receive waveguide, which is configured to convey the optical radiation received by the optical transducer to the receiver.

In a disclosed embodiment, the at least one tap includes a first tap coupled to convey a first part of the coherent radiation from the bus to the transmit waveguide and a second tap coupled to convey a second part of the coherent radiation to the receiver for mixing with the received optical radiation. In one embodiment, the optical bus includes a single waveguide to which both the first and second taps are coupled. In another embodiment, the optical bus includes a first waveguide, to which the first tap is coupled, and a second waveguide, to which the second tap is coupled.

In one embodiment, in each cell, the optical transducer includes a first transducer element configured to couple the coherent radiation out of the transmit waveguide toward the target and a second transducer element configured to couple the optical radiation that is incident on the optical transducer into the receive waveguide.

Alternatively or additionally, each cell includes a coupler configured to couple the coherent radiation from the transmit waveguide to the optical transducer for transmission toward the target and to couple the optical radiation that is incident on the optical transducer into the receive waveguide. In one embodiment, the coherent radiation conveyed by the transmit waveguide has a first polarization, and the optical transducer is configured to receive and convey to the coupler the incident optical radiation of both the first polarization and a second polarization, orthogonal to the first polarization, and the coupler is configured to couple the optical radiation received with both the first and second polarizations to the receiver.

In a disclosed embodiment, the coupler includes a polarization beamsplitter rotator, which is configured to rotate the received optical radiation with the second polarization to the first polarization. In one embodiment, the optical transducer includes an edge coupler, and the polarization beamsplitter rotator is integrated with the edge coupler.

In another embodiment, the optical transducer includes a grating coupler, which includes a first grating coupled to the transmit waveguide and a second grating coupled to the receive waveguide. In a disclosed embodiment, the first grating is configured to couple the coherent radiation between the transmit waveguide and a first range of angles in a space over the substrate, and the second grating is configured to couple the optical radiation that is incident on the grating coupler within a second range of angles, different from the first range, into the receive waveguide.

In an alternative embodiment, the optical transducer is configured to receive and convey to the receiver the incident optical radiation of both a first polarization and a second polarization, orthogonal to the first polarization, and the receiver includes a first mixer and a first detector for mixing and detecting the received optical radiation of the first polarization and a second mixer and a second detector for mixing and detecting the received optical radiation of the second polarization.

In some embodiments, the optical transducer includes an edge coupler. In other embodiments, the optical transducer includes a grating coupler.

In some embodiments, the signal output by the receiver in each sensing cell includes a beat frequency responsive to a range of the target from the device. In a disclosed embodiment, the receiver in each sensing cell includes an optical hybrid and a pair of detectors, which are coupled to receive in-phase (I) and quadrature (Q) components of the mixed radiation and to output corresponding I and Q components of the electrical signal.

There is also provided, in accordance with an embodiment of the invention, an optical coupler, including a planar substrate and first and second waveguides disposed on the substrate. A first grating disposed on the substrate is coupled to diffract first optical radiation between the first waveguide and a first range of angles in a space over the substrate. A second grating is disposed on the substrate over the first grating and coupled to diffract second optical radiation between the second waveguide and a second range of angles, different from the first range, in a space over the substrate.

In a disclosed embodiment, the first and second ranges of angles are disjoint in a far field of the first and second gratings.

Additionally or alternatively, an optical element is mounted over the substrate and configured to focus both the first and second optical radiation over the first and second ranges of angles.

There is additionally provided, in accordance with an embodiment of the invention, an optoelectronic apparatus, including a carrier substrate and a dual folding mirror mounted on the carrier substrate and including first and second reflecting surfaces disposed at opposite angles relative to a normal to the carrier substrate. A first sensing device includes a first planar substrate disposed on the carrier substrate with a first edge of the first planar substrate in proximity to the first reflecting surface, and a first array of first sensing cells disposed on the first planar substrate and including respective first edge couplers disposed along the first edge of the first planar substrate so as to couple optical radiation between the first sensing cells and the first reflecting surface. A second sensing device includes a second planar substrate disposed on the carrier substrate with a second edge of the second planar substrate in proximity to the second reflecting surface, and a second array of second sensing cells disposed on the second planar substrate and including respective second edge couplers disposed along the second edge of the second planar substrate so as to couple optical radiation between the second sensing cells and the second reflecting surface In a disclosed embodiment, the dual folding mirror has a triangular profile, wherein the first and second reflecting surfaces are oriented respectively at +45° and −45° relative to the normal.

Additionally or alternatively, the first and second edges are both parallel to a common axis, wherein the first and second edge couplers are disposed along the first and second edges with a predefined pitch between the edge couplers, and wherein the second edge couplers are offset along the common axis by half the predefined pitch relative to the first edge couplers.

Further additionally or alternatively, the first and second sensing cells include respective receivers, which are coupled to the edge couplers by waveguides disposed on the first and second planar substrates, wherein the receivers have respective widths greater than the predefined pitch and are disposed at different, respective distances from the first and second edges.

In some embodiments, the first and second sensing cells include optical transceiver cells, which are configured to direct coherent radiation through the respective first and second edge couplers via the dual folding mirror toward a target, to receive optical radiation from the target via the dual folding mirror through the respective first and second edge couplers, to mix a part of the coherent radiation with the optical radiation received through the first and second edge couplers, and to output an electrical signal responsively to the mixed radiation.

In a disclosed embodiment, the first and second sensing devices include respective optical buses disposed on the first and second planar substrates and configured to convey the coherent radiation through the bus, and the first and second sensing cells include respective taps coupled to extract a portion of the coherent radiation propagating through the optical buses for transmission toward the target and mixing with the received optical radiation.

Additionally or alternatively, the first and second edge couplers define respective optical apertures of the first and second sensing cells, and the apparatus includes one or more optical elements configured to image the optical apertures onto the target. In a disclosed embodiment, the one or more optical elements are configured to image the optical apertures onto the target along an optical axis, and the apparatus includes a scanner, which is configured to shift at least one of the optical elements in a direction transverse to the optical axis so as to scan the imaged optical apertures across the target. Additionally or alternatively, the scanner is configured to shift the carrier substrate in a direction transverse to the optical axis so as to scan the imaged optical apertures across the target.

Further additionally or alternatively, the apparatus includes a rotating mirror, which is disposed between the dual folding mirror and the target and is configured to scan the imaged optical apertures across the target.

There is further provided, in accordance with an embodiment of the invention, an optoelectronic apparatus, which includes a sensing device, including a planar substrate and an array of sensing cells disposed on the substrate and including respective optical transducers, which are configured to couple optical radiation between the sensing cells and a target external to the substrate, thereby defining respective optical apertures of the sensing cells, and which are located at respective nodes on respective rows and columns of a two-dimensional rectangular grid such that no more than half the nodes on the respective rows and columns are occupied by the optical transducers. A scanner is configured to scan the optical apertures across the target along at least the rows of the grid so that the optical apertures are projected successively onto respective sequences of multiple nodes in the rectangular grid on the target.

In some embodiments, the apparatus includes one or more optical elements, which are configured to form an image of the rectangular grid on the target.

In a disclosed embodiment, the scanner is configured to scan the optical apertures along both the rows and the columns of the rectangular grid. Additionally or alternatively, the scanner is configured to vary a speed of scanning the optical apertures over different areas of the target. Further additionally or alternatively, the scanner is configured to vary a density of the nodes of the grid onto which the optical apertures are projected over different areas of the target.

In a disclosed embodiment, the apparatus includes a controller, which is configured to actuate the sensing cells selectively as the optical apertures are scanned across the target so as to vary a density of the nodes of the grid where the optical radiation is sensed by the sensing cells over different areas of the target.

There is moreover provided in accordance with an embodiment of the invention, an optoelectronic apparatus, which includes a sensing device, including at least one planar substrate and an array of sensing cells disposed on the at least one planar substrate and including respective optical transducers, which are configured to couple optical radiation between the cells and a target external to the substrate, thereby defining respective optical apertures of the cells, which are arranged in at least one row along a row axis. A scanner includes a mirror which is configured to project and scan the optical apertures across the target while rotating about a rotational axis that is oriented at an oblique angle relative to the row axis.

In a disclosed embodiment, the optical transducers include edge couplers, which are disposed along an edge of the at least one planar substrate.

Additionally or alternatively, the at least one planar substrate includes a plurality of planar substrates, having respective rows of the optical transducers disposed thereon. In one embodiment, the planar substrates are stacked along a direction perpendicular to the rows of the optical transducers. In another embodiment, the apparatus includes a beamsplitter cube, wherein the planar substrates are mounted on different, respective faces of the beamsplitter cube.

There is furthermore provided, in accordance with an embodiment of the invention, an optoelectronic apparatus, including a focusing element having an optical axis and a first array of optical cells, having respective optical apertures. A second array of reflectors are disposed along the optical axis at different, respective distances from the focusing element. Each reflector is configured to deflect radiation propagating between a respective one of the optical apertures of the optical cells and the focusing element. A third array of path equalizers are configured to adjust respective effective focal lengths between the focusing element the optical apertures and so that all the effective focal lengths are equal.

Typically, the reflectors, except for one reflector farthest from the focusing element, are partial reflectors. In one embodiment, the reflectors, except for the one reflector farthest from the focusing element, are dichroic reflectors.

In a disclosed embodiment, the path equalizers include pedestals of different, respective heights, on which the optical cells are respectively mounted.

Alternatively or additionally, the path equalizers include blocks of transparent dielectric material of different, respective thicknesses, which are disposed between the optical cells and the reflectors.

There is also provided, in accordance with an embodiment of the invention, apparatus for sensing, including an array of transceiver cells, which have respective optical apertures, defining respective fields of view of the transceiver cells, and are configured to transmit respective beams of coherent radiation toward a target and receive the coherent radiation reflected from the target through the respective optical apertures. A scanner is configured to scan the fields of view of the transceiver cells across the target. A processor is configured to control the transceiver cells and the scanner so as to scan the fields of view of the transceiver cells over a target area in a first scan at a first resolution, to process signals output by the transceiver cells during the first scan in order to identify a region of interest within the target area, to control the transceiver cells and the scanner so as to scan the fields of view of the transceiver cells selectively across the region of interest in a second scan at a second resolution, which is finer than the first resolution, and to process the signals output by the transceiver cells during the second scan in order to produce a three-dimensional (3D) map of the region of interest.

There is additionally provided, in accordance with an embodiment of the invention, a method for sensing, which includes providing an array of transceiver cells, which have respective optical apertures, defining respective fields of view of the transceiver cells, and are configured to transmit respective beams of coherent radiation toward a target and receive the coherent radiation reflected from the target through the respective optical apertures. The fields of view of the transceiver cells are scanned across a target area in a first scan at a first resolution. Signals output by the transceiver cells during the first scan are processed in order to identify a region of interest within the target area. The fields of view of the transceiver cells are scanned selectively across the region of interest in a second scan at a second resolution, which is finer than the first resolution. The signals output by the transceiver cells during the second scan are processed in order to produce a three-dimensional (3D) map of the region of interest.

In some embodiments, processing signals output by the transceiver cells during the first scan includes identifying lateral boundaries of the region of interest. In one embodiment, scanning the fields of view in the first scan includes scanning the fields of view at a first scan speed in the first scan, and scanning the fields of view in the second scan includes scanning the fields of view between the identified lateral boundaries at a second scan speed, less than the first scan speed, in the second scan. In a disclosed embodiment, processing signals output by the transceiver cells during the first scan includes identifying a depth of the region of interest, and scanning the fields of view at the second scan speed includes setting the second scan speed responsively to the identified depth.

Additionally or alternatively, scanning the fields of view in the first scan includes receiving the signals only from a first set of the transceiver cells in the first scan, and scanning the fields of view in the second scan includes receiving the signals in the second scan from a second set of the transceiver cells, which is a superset of the transceiver first set that are contained within the identified lateral boundaries.

Additionally or alternatively, processing signals output by the transceiver cells during the first scan includes identifying a depth of the region of interest. In a disclosed embodiment, scanning the fields of view in the first scan includes transmitting the beams of coherent radiation with a first intensity in the first scan, and scanning the fields of view in the second scan includes selecting a second intensity, greater than the first intensity, responsively to the identified depth, and transmitting the beams of coherent radiation at the second intensity while scanning over the region of interest in the second scan. Additionally or alternatively, scanning the fields of view in the first scan includes receiving the signals from the transceiver cells over a first integration time in the first scan, and scanning the fields of view in the second scan includes receiving the signals from the transceiver cells over a second integration time, greater than the first integration time, while scanning over the region of interest in the second scan.

There is further provided, in accordance with an embodiment of the invention, a method for sensing, which includes conveying coherent radiation through an optical bus including at least one waveguide disposed on a substrate. An array of sensing cells is disposed on the substrate along the optical bus, each sensing cell including at least one tap coupled to extract a portion of the coherent radiation propagating through the optical bus. Optical radiation is coupled between each sensing cell and a target external to the substrate via an optical transducer associated with the sensing cell. The coherent radiation extracted by the tap in each sensing cell is mixed with the optical radiation received by the optical transducer. An electrical signal is output from each of at least some of the sensing cells responsively to the mixed radiation.

There is moreover provided, in accordance with an embodiment of the invention, a method for coupling, which includes providing first and second waveguides disposed on a planar substrate. A first grating on the substrate is coupled to diffract first optical radiation between the first waveguide and a first range of angles in a space over the substrate. A second grating is disposed on the substrate over the first grating and is coupled to diffract second optical radiation between the second waveguide and a second range of angles, different from the first range, in a space over the substrate.

There is furthermore provided, in accordance with an embodiment of the invention, a method for optical sensing, which includes mounting on a carrier substrate a dual folding mirror including first and second reflecting surfaces disposed at opposite angles relative to a normal to the carrier substrate. A first sensing device, placed on the carrier substrate, includes a first sensing device including a first planar substrate and a first array of first sensing cells disposed on the first planar substrate and including respective first edge couplers disposed along a first edge of the first planar substrate, such that the first edge of the first planar substrate is in proximity to the first reflecting surface, whereby the first edge couplers couple optical radiation between the first sensing cells and the first reflecting surface. A second sensing device, placed on the on the carrier substrate, includes a second planar substrate and a second array of second sensing cells disposed on the second planar substrate and including respective second edge couplers disposed along a second edge of the second planar substrate, such that the second edge of the second planar substrate is in proximity to the second reflecting surface, whereby the second edge couplers couple optical radiation between the second sensing cells and the second reflecting surface There is also provided, in accordance with an embodiment of the invention, a method for optical sensing, which includes providing an array of sensing cells on a planar substrate. The sensing cells include respective optical transducers, which couple optical radiation between the sensing cells and a target external to the substrate, thereby defining respective optical apertures of the sensing cells, and which are located at respective nodes on respective rows and columns of a two-dimensional rectangular grid such that no more than half the nodes on the respective rows and columns are occupied by the optical transducers. The optical apertures are scanned across the target along at least the rows of the grid so that the optical apertures are projected successively onto respective sequences of multiple nodes in the rectangular grid on the target.

There is additionally provided, in accordance with an embodiment of the invention, a method for optical sensing, which includes providing an array of sensing cells disposed on at least one planar substrate and including respective optical transducers, which couple optical radiation between the cells and a target external to the substrate, thereby defining respective optical apertures of the cells, which are arranged in at least one row along a row axis. The optical apertures are projected and scanned across the target using a mirror, which rotates about a rotational axis that is oriented at an oblique angle relative to the row axis.

There is further provided, in accordance with an embodiment of the invention, a method for optical alignment, which includes providing a focusing element having an optical axis and a first array of optical cells, having respective optical apertures. A second array of reflectors is disposed along the optical axis at different, respective distances from the focusing element, such that each reflector deflects radiation propagating between a respective one of the optical apertures of the optical cells and the focusing element. A third array of path equalizers are applied to adjust respective effective focal lengths between the focusing element the optical apertures and so that all the effective focal lengths are equal.

The present invention will be more fully understood from the following detailed description of the embodiments thereof, taken together with the drawings in which:

BRIEF DESCRIPTION OF THE DRAWINGS

FIG. 3 is a block diagram that schematically illustrates an integrated optical transceiver cell, in accordance with an embodiment of the invention;

FIGS. 4 and 5 are block diagrams that schematically illustrate integrated optical receivers, in accordance with embodiments of the invention;

FIGS. 8 and 9 are block diagrams that schematically illustrate integrated optical transceiver cells, in accordance with further embodiments of the invention;

FIG. 21 is a schematic frontal view of a target irradiated by an optical sensing system over a sequence of scan times, in accordance with an embodiment of the invention;

FIGS. 25A, 25B and 25C are schematic frontal views of a target irradiated by an optical sensing system over a sequence of scan times, in accordance with an embodiment of the invention;

FIG. 28A is a schematic pictorial view of an optical sensing system, in accordance with still another embodiment of the invention;

FIGS. 28B and 28C are schematic top and side views, respectively, of an optical module used in the optical sensing system of FIG. 28A, in accordance with an embodiment of the invention;

DETAILED DESCRIPTION OF EMBODIMENTS

Overview

Figure 1:
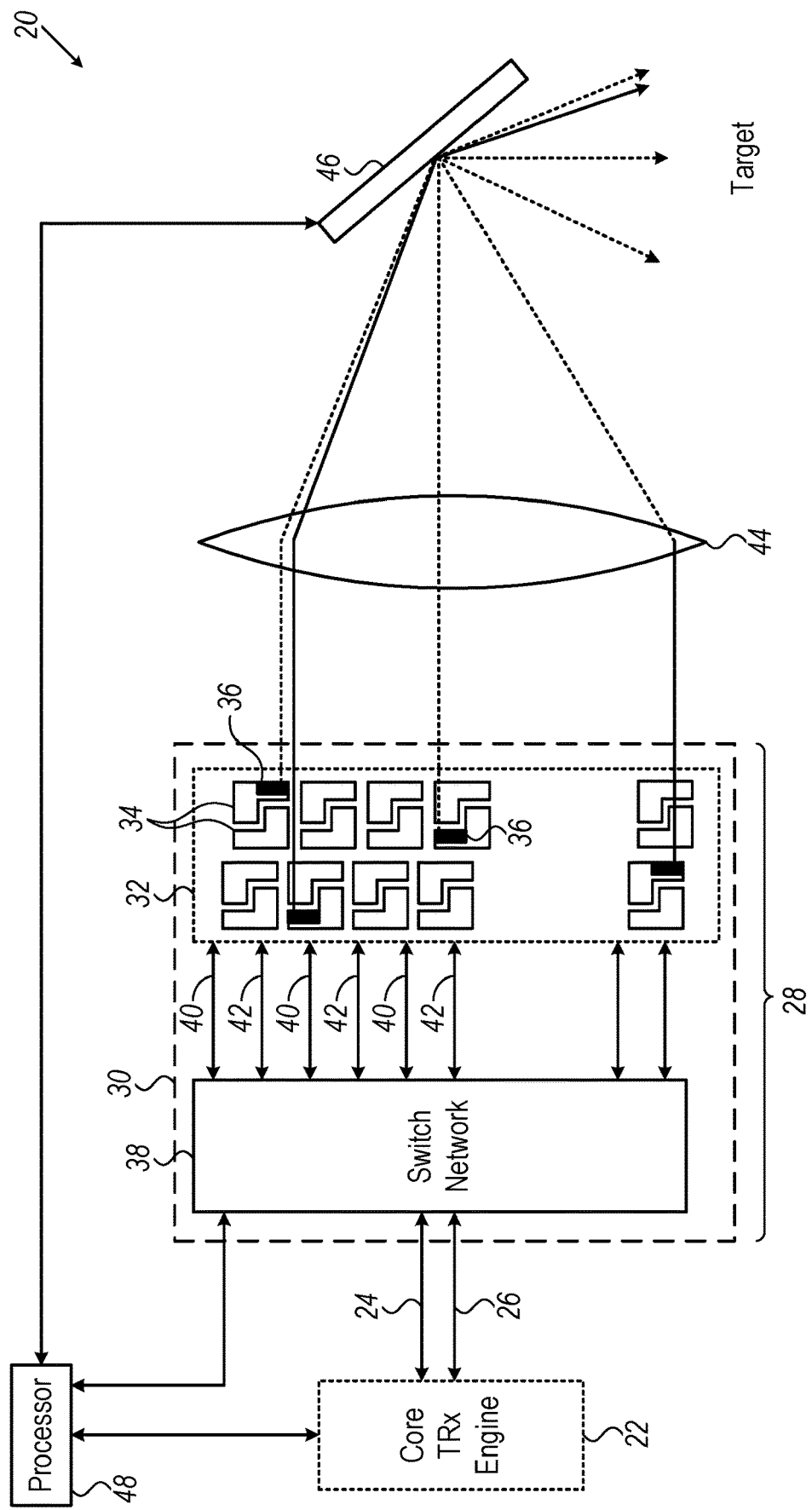
FIG. 1 is a block diagram that schematically illustrates an optical sensing system, in accordance with an embodiment of the invention.

As noted earlier, in coherent sensing applications, such as OCT and CW LiDAR, a coherent beam is transmitted toward a target, and the reflected radiation is sensed and processed coherently with the transmitted radiation. To sense the properties of the target with high resolution, the area of interest should be probed densely, either by scanning the transmitted beam over the area or by transmitting and sensing an array of multiple beams simultaneously. Scanning solutions, however, typically suffer from low throughput. Arrays of transmitters and receivers can improve throughput, but their resolution is limited by the pitches of the arrays, which are, in turn, limited by the sizes of the transmitters and receivers themselves.

Embodiments of the present invention address these problems by providing transceiver arrays and scanning systems that are able to scan a target with high resolution and high throughput. These embodiments use arrays of photonic sensing cells. In some embodiments, the arrays comprise transceiver cells, wherein each cell includes optical and optoelectronic components both for transmitting a beam of radiation and for receiving and detecting reflected radiation, along with ancillary electronics. In other embodiments, the cells may comprise components only for receiving and detection of radiation.

To reduce the size, power and complexity requirements of the sensing cells, the beams that are to be transmitted and/or mixed with the received radiation for coherent detection may be generated and modulated centrally, by a core transceiver engine, and then multiplexed among the sensing cells. A scanner, such as an optomechanical scanning device, scans the fields of view of all the cells over the area of interest so that the area is covered densely—with resolution finer than the physical pitch of the array of sensing cells—and with high throughput. The multiplexing and scanning may be controlled to tailor the scan area and resolution to application requirements. A variety of array geometries and scan patterns that can be used for these purposes are described below.

In the disclosed embodiments, the sensing cells themselves are typically produced using photonic integrated circuit (PIC) technology. These cells are designed to meet application requirements, such as the sensing mode and sensitivity, the mode of input/output coupling (for example, vertically or through the edge of the chip, via a grating or via a mirror), and wavelength characteristics (spectral range, and single- or multiple-wavelength sensing). A variety of representative embodiments are described below.

A number of applications of the present sensing cell arrays and scanning systems are described below by way of example. The principles of the present embodiments, however, may be readily extended and adapted to other applications involving multi-beam sensing. Furthermore, although the disclosed embodiments are directed to optical sensing, in the visible, infrared, or ultraviolet range, the principles of the present invention may alternatively be applied, mutatis mutandis, in other spectral ranges, such as microwave and millimeter-wave radiation. All such alternative applications are considered to be within the scope of the present invention.

Sensing Cell Arrays with Optical Buses

One of the challenges in producing compact coherent sensing arrays is to provide coherent optical radiation to all the cells of the array, with optical quality and power level sufficient to achieve high resolution and high signal/noise ratio (SNR). For some applications, such as optical coherence tomography (OCT) and continuous-wave (CW) LiDAR, the optical radiation should also be modulated. Incorporating an individual laser source in each cell increases the cell footprint and power dissipation substantially and may not achieve the desired optical quality.

To overcome these limitations, some embodiments of the present invention use a core transceiver (TRx) engine to supply coherent radiation to the entire array of sensing cells. One or more optical buses, comprising waveguides disposed on the same planar substrate as the sensing cells, are used to distribute the coherent radiation to the cells. each cell comprises at least one tap, which is coupled to extract a portion of the coherent radiation propagating through the optical bus. An optical transducer, such as a grating coupler or edge coupler, in each cell couples optical radiation between the cell and a target external to the substrate. A receiver mixes coherent radiation extracted by the tap with optical radiation received by the optical transducer and outputs an electrical signal in response to the mixed radiation. A variety of different bus and cell structures are described hereinbelow.

FIG. 1 is a block diagram that schematically illustrates an optical sensing system 20, in accordance with an embodiment of the invention.

In system 20, a core TRx engine 22 comprises one or more laser light sources, along with photonic and electronic circuit components for control, modulation, and distribution of the coherent radiation generated by the light sources. TRx engine 22 can implement a variety of different modulation schemes, such as amplitude modulation, frequency modulation and/or phase modulation, and including chirped modulation for use in frequency-modulated continuous wave (FMCW) LIDAR and phase-modulated continuous wave (PMCW) LIDAR. The modulation may be applied by controlling the drive current supplied to the laser or lasers. Alternatively or additionally, the modulation may be applied externally, for example by optical modulation of the laser beam. TRx engine 22 is connected by one or more optical waveguides 24, and possibly also an electrical bus 26, to an optoelectronic sensing device 28, which is formed on a substrate 30.

In the embodiments described below, device 28 is fabricated using photonic integrated circuit (PIC) technology, and substrate 30 comprises a silicon die, for example in a silicon on insulator (SOI) configuration. Alternatively, substrate 30 may comprise other sorts of semiconductor or dielectric materials. Core TRx engine 22 may be disposed on substrate 30, as well, in which cases waveguides 24 and bus 26 may conveniently be formed on substrate 30, for example by photolithographic processes. Alternatively, core TRx engine 22 may be coupled to substrate 30 via one or more edge couplers or one or more grating couplers (not shown). Further alternatively, waveguides 24 and bus 26 may comprise optical fibers and conductive wires, respectively.

Device 28 comprises an array 32 of sensing cells 34 formed on substrate 30. Each sensing cell 34 comprises an optical transducer 36, which couples light in and out of the cell, along with photonic and electronic components, as shown in detail in the figures that follow. Sensing cells 34 may all be of the same type, or alternatively, device 28 may include two or more different types of sensing cells. In some embodiments, sensing cells 34 comprise transceiver (TRx) cells, including photonic components for both transmission and reception of light; and in this case, transducers 36 both transmit light toward a target and receive light reflected from the target. Alternatively or additionally, sensing cells 34 may comprise only receiving components, which receive light reflected from a target following transmission of the light through other channels (not shown).

Sensing cells 34 have respective fields of view, which are defined by the respective optical apertures of optical transducers 36 and by focusing optics 44, which project the optical apertures onto a target. A scanner 46 scans the fields of view over the target. (Although scanner 46 is shown in FIG. 1, for the sake of simplicity, to be scanning only in a direction parallel to the longitudinal axis of array 32, scanner 46 typically scans in a perpendicular direction or in two directions.) Each transducer 36 emits (and receives) a cone of light that is collimated by optics 44, and the resulting beam from each transducer is projected into a different angle in the field of view. In addition, scanner 46 can scan the beams to control the density of coverage of the field of view of system 20, including varying the density of coverage in different areas of the field. In this manner, even when the fields of view of transducers themselves cover the target only sparsely, the density of coverage will be filled in as desired over the entire target of areas of interest within the target.

In the pictured embodiments, scanner 46 comprises one or more rotating mirrors, which scan over the target along one or two scan axes. Alternatively or additionally, the scanner may comprise a motion assembly (shown in FIG. 20A), which shifts optics 44 in a transverse direction, or any other suitable type of mechanical, optical, or wavelength-based scanner, for example. Generally speaking, scanner 46 may operate by mechanical scanning (for example using a galvanometer mirror, or MEMS mirrors with one or two scanning directions); movement of a lens and/or sensor (for example using a piezoelectric actuator, VCM, or thermal scanner); wavelength scanning in combination with a dispersive element, such as a prism or grating; polarization-based scanning; phased array scanning; modulation of a liquid lens or mirror; liquid crystal on silicon (LCOS) scanning; digital micromirror devices; or any other suitable mechanism that is known in the art.

A switch network 38 on substrate 30 distributes light received through waveguides 24 among multiple optical buses 40, which comprise waveguides coupled to deliver the light to different, respective sets of sensing cells 34. Switch network 38 also couples electrical signals between electrical bus 26 and electrical buses 42, for transfer of the electrical signals to and from sensing cells 34. Switch network 38 may comprise an active optical network, comprising optoelectronic components which select the buses 40 to which the light is to be distributed. Alternatively or additionally, switch network 38 may comprise a passive optical splitter array.

The use of active optical switching adds complexity to device 28 but enables the optical energy provided through waveguides 24 to be distributed selectively among sensing cells 34. This sort of active, switched network can be used to select individual sensing cells or groups of sensing cells to be activated in scanning over a target. In this manner, for example, certain rows of a raster scan can be selected for sensing in different areas of the target; and the spacing between raster rows can be varied depending on the desired resolution. Thus, the available optical energy can be concentrated in the sensing cells in locations corresponding to regions of interest in the target.

To summarize, the scheme shown generally in FIG. 1 enables a flexible choice of scanning characteristics and scan pattern by appropriate choices of the geometrical layout of array 32, scanning of the fields of view of sensing cells 34 by scanner 46, and switch network 38. The operation of system 20 can thus be controlled in both the spatial and temporal dimensions to enrich the information content of the projected and received images. A given spatial location can thus receive information from several different modalities, multiplexed by temporal scanning. In addition, scanning in any one dimension effectively projects points along the other dimension along the temporal axis, and thus opens up possibilities of spatio-temporal multiplexing with enriched collection of information as a result. Furthermore, the interplay between fast switching (optical and/or electrical) by switch network 38 and the scanning modalities described above creates additional scanning possibilities, such as varying the dwell time on the target dynamically as needed, as well as adaptive control of resolution and frame rate and configurable definition of regions of interest.

A processor 48 controls the operation of system 20 and receives signals output by sensing cells 34 in response to light received by device 28. Processor 48 typically comprises a general-purpose microprocessor, with suitable analog and digital interfaces for controlling and receiving signals from the components of system 20. Alternatively or additionally, processor 48 may comprise special-purpose digital logic and other hardware components, which may be hard-wired or programmable. Processor 48 processes the signals output by sensing cells 34 in order to reconstruct features of the target. For example, processor 48 may generate a depth map of the target using techniques of optical coherence tomograph (OCT) for short-range targets or CW LIDAR for longer-range targets.

In some embodiments, processor 48 actuates sensing cells 34 selectively, i.e., the processor receives signals from different sensing cells in different sweeps of scanner 46 or even during a single sweep. As noted earlier, when switch network 38 comprises an active optical network, it can be controlled in this context to direct the light from core TRx engine 22 to the sensing cells that are active at any given instant and thus use the available optical power more efficiently. By selective activation of sensing cells 34, processor 48 can vary the resolution of a scan and/or concentrate sensing resources in a certain region of interest of the target. Additionally or alternatively, processor 48 can control parameters including the range and speed of scanner 46, the intensity of the beams transmitted toward target, and the integration time of sensing cells 34 in order to adjust the range, resolution, and SNR of any given scan. Details of this functionality are described further hereinbelow with reference to FIGS. 34-36.

Figure 2:
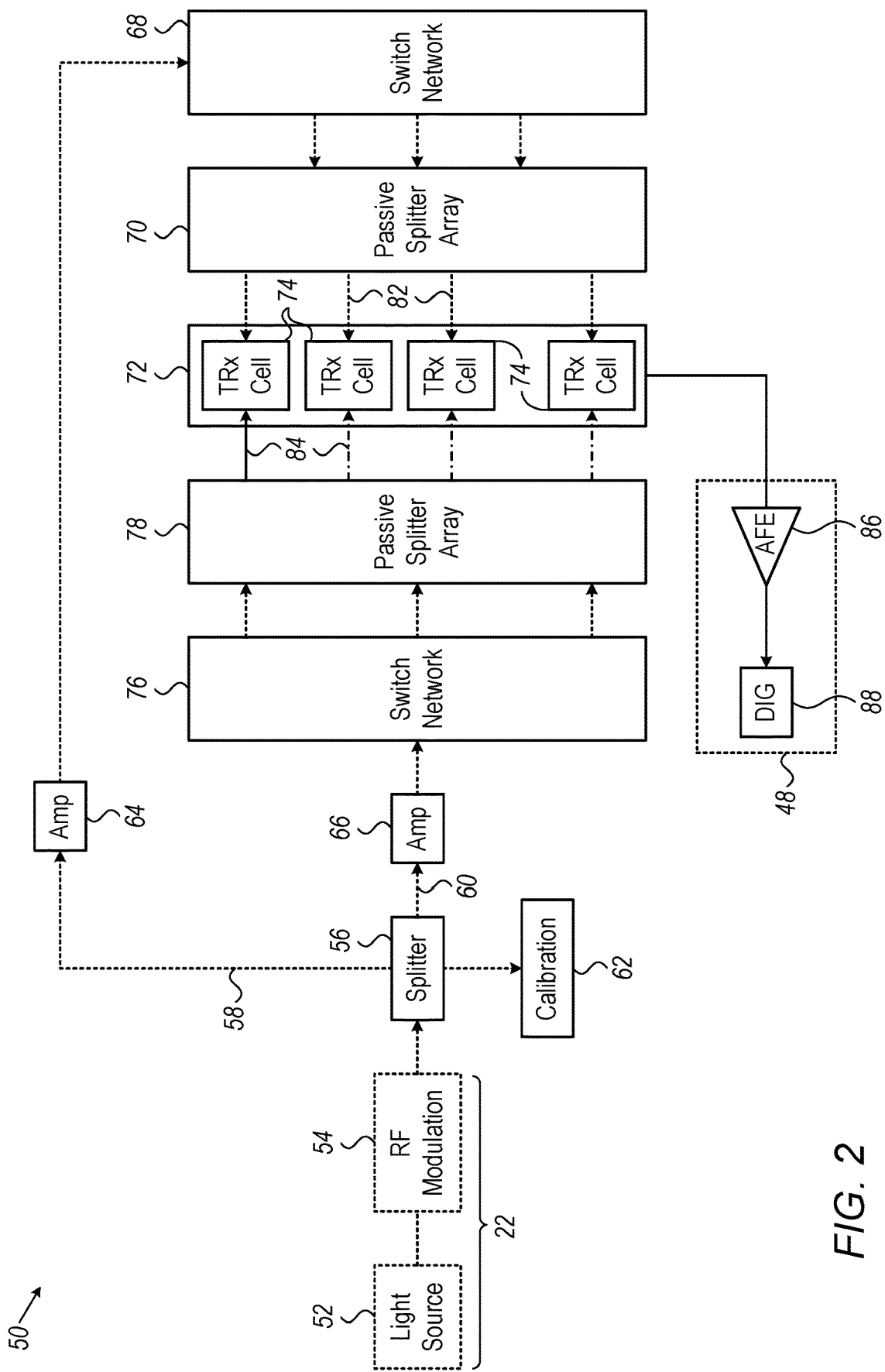
FIG. 2 is a block diagram that schematically shows details of an optical sensing system, in accordance with an embodiment of the invention.

FIG. 2 is a block diagram that schematically shows details of an optical sensing system 50, in accordance with an embodiment of the invention. System 50 is similar in its construction and principles of operation to system 20 and is described here to illustrate particular implementation features. Elements of system 50 with functionality similar to that of corresponding elements of system 20 are labeled with the same indicator numbers.

Optical radiation emitted by a light source 52 is modulated by an RF modulator 54, for example to apply a frequency chirp for purposes of frequency-modulated CW (FMCW) LIDAR. A splitter 56 splits the modulated beam between a reference arm 58, a signal arm 60, and a calibration unit 62. The beams in reference arm 58 and/or signal arm 60 may be amplified by optical amplifiers 64, 66, such as semiconductor optical amplifiers (SOAs). The beam in reference arm 58 is routed by a switch network 68 to a subset of the passive splitters in a passive splitter array 70, and is then fed as a local oscillator (LO) beam via optical buses 82 to a subset of TRx cells 74 in an array 72.

The beam in signal arm 60 is routed by a switch network 76, through a passive splitter array 78 via optical buses 84, typically (although not necessarily) to the same subset of TRx cells 74 as the LO beam. Switch networks 70 and 76 operate together, under the control of processor 48, to select and activate the desired subsets of TRx cells 74. The selected TRx cells 74 transmit the beams provided by buses 84 toward the target and then receive radiation reflected from the target and mix the received radiation with the LO beams provided by buses 82. The resulting electrical signals are amplified and filtered by an analog front end (AFE) 86 and then input to a digital processing block 88. Digital processing block 88 includes, for example, an analog/digital converter (ADC), which converts the analog signals to digital sample; a digital signal processor (DSP), which processes the signals to extract data, such as depth and velocity information; and a controller, such as processor 48 (FIG. 1), which orchestrates system operation and may include switching controls, scanning controls, and laser controls, for example. In FMCW sensing, for example, digital processing block 88 extracts the beat frequencies of the signals and thus measures the ranges and velocities of points on the target. To reduce the cost and power consumption of system 50 the processing resources of AFE 86 and/or digital processing block 88 may be multiplexed among TRx cells 74, as described further hereinbelow with reference to FIG. 32.

Calibration unit 62 extracts a phase-synchronized clock signal from the modulated beam that it receives from splitter 62. Calibration unit 62 may also monitor transmission parameters, such as modulation, coherence, power, etc.

FIG. 3 is a block diagram that schematically illustrates an integrated optical transceiver cell 90, in accordance with an embodiment of the invention. Transceiver cell 90, as well as the transceiver and receiver cells shown in the figures that follow, may be used in place of sensing cells 34 in FIG. 1 or TRx cells 74 in FIG. 2.

Cell 90 comprises a pair of taps 92 and 94, which extract respective portions of the coherent radiation propagating in a bus 96 for input to a transmit waveguide 98 and a LO waveguide 100, respectively. Bus 96 may comprise a single waveguide to which both taps are connected, or multiple waveguides, carrying the Tx and LO beams in separate channels. In an alternative embodiment (not shown in the figures), cell 90 may comprise a single tap to bus 96, with an internal splitter (not shown) to split off a small part of the Tx beam to serve as the LO beam.

A photonic circuit 102 in cell 90 comprises a coupler 104, which passes the outgoing coherent radiation via a bidirectional waveguide 106 to an optical transducer 108, such as a grating coupler or edge coupler, for transmission toward the target. For example coupler 104 may comprise a directional coupler or a beamsplitting coupler, such as a polarization beamsplitter rotator (PB SR).

Transducer 108 also receives incoming radiation from the target and conveys the incoming radiation via waveguide 106 and coupler 104 to a receive waveguide 110. Radiation rejected by coupler 104 may be conveyed to a photodiode 112 for termination and monitoring. A receiver 114 mixes the coherent radiation from LO waveguide 100 with the incoming radiation received through receive waveguide 110 and generates a corresponding electrical output signal.

FIG. 4 is a block diagram that schematically illustrates an implementation of receiver 114, in accordance with embodiments of the invention. A mixer 120, such as a 2×2 optical coupler, receives and mixes the coherent beams from LO waveguide 100 and receive (Rx) waveguide 110. The mixed optical signal is passed to a balanced photodiode detector 122, comprising a pair of photodiodes 124 and an analog front end (AFE) circuit 126, which outputs a resulting electrical signal. Assuming the coherent beam carried by bus 96 to be suitably modulated, for example with a frequency chirp, the electrical output signal will comprise a beat frequency indicative of the range and velocity of the target.

FIG. 5 is a block diagram that schematically illustrates a receiver 130, which can be substituted for receiver 114 in transceiver cell 90, in accordance with embodiments of the invention. In this case, the coherent beams from LO waveguide 100 and receive (Rx) waveguide 110 are input to a 90° optical hybrid 132, which contains two mixers (not shown), with a 90° phase shift applied to one of the beams that is input to one of the mixers. Thus, one of the mixers outputs an in-phase (I) mixed optical component to a first balanced photodiode detector 134, while the other mixer outputs a quadrature (Q) mixed optical component to a second balanced photodiode detector 136. Detectors 134 and 136 output corresponding I and Q components of the electrical output signal. This I/Q detection configuration is useful in improving the signal/noise ratio (SNR) and linearity of beat frequency detection.

In the embodiments that are described below, the receivers may be of the single-output type shown in FIG. 4 or the I/Q type shown in FIG. 5. Alternatively, other suitable receiver configurations may be used, depending on application requirements.

Figures 6, 7:
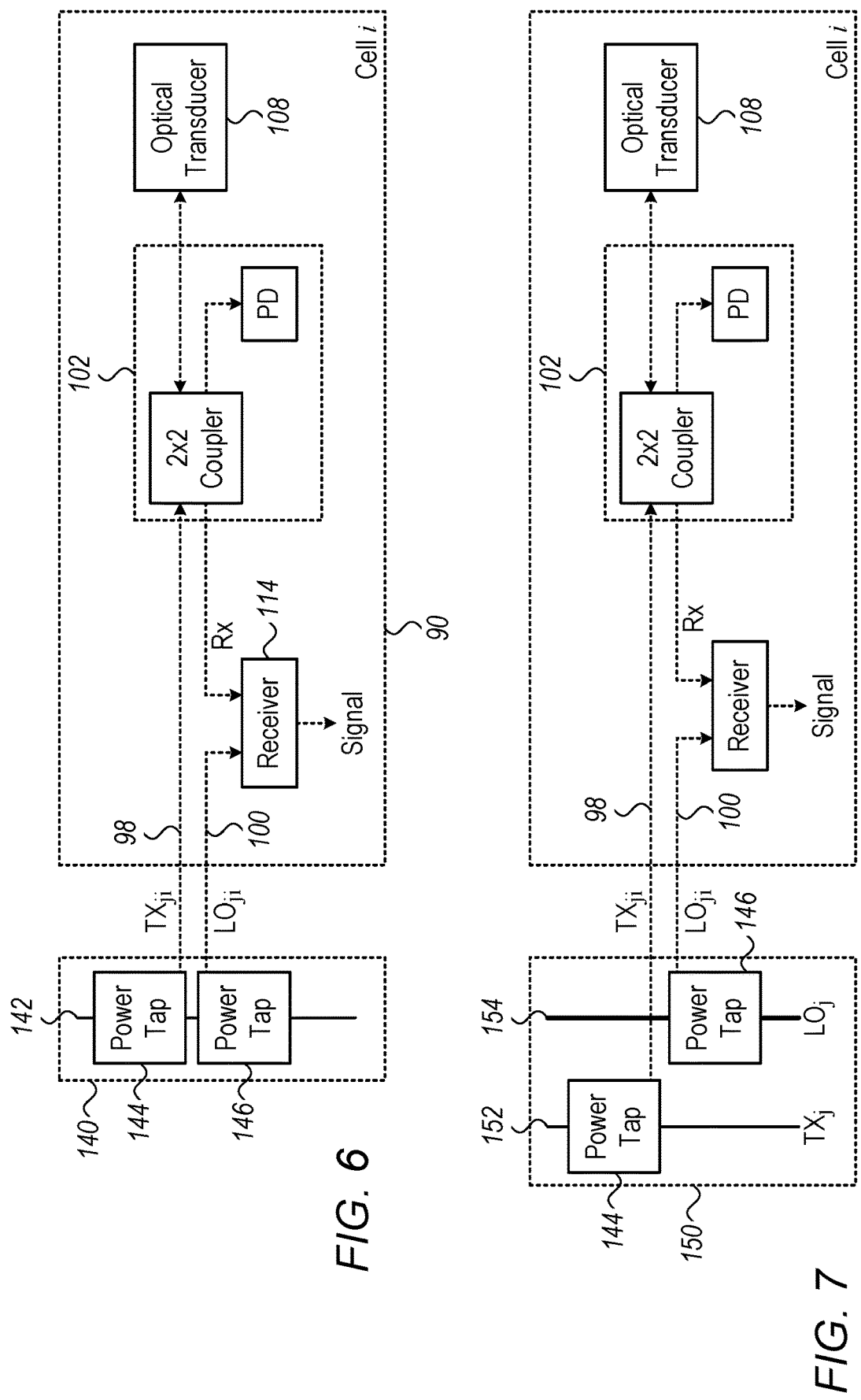
FIGS. 6 and 7 are block diagrams that schematically show details of an integrated optical transceiver array, in accordance with embodiments of the invention.

FIG. 6 is a block diagram that schematically shows details of the connections of optical transceiver cell 90 to an optical bus 140 in an integrated optical transceiver array, in accordance with an embodiment of the invention. Bus 140 in this embodiment comprises a single waveguide 142, which conveys coherent optical radiation from core TRx engine 22 (FIG. 1), for example. A transmit tap 144 extracts a part of the radiation propagating in waveguide 142 for transmission via transmit waveguide 98 and optical transducer 108 toward the target. A LO tap 146 extracts another part of the radiation for input via LO waveguide 100 to receiver 114.

Considering the different power requirements of the transmitted and LO beams, transmit tap 144 is typically configured to extract a much larger fraction of the propagating energy than LO tap 146. Even tap 144, however, may extract only a small fraction of the propagating energy in waveguide 142 so that bus 140 can also supply other transceiver cells in the array. Although only a single bus 140 is shown in FIG. 6, the optical transceiver array may comprise multiple buses of this sort, each serving a different group of transceiver cells 90.

FIG. 7 is a block diagram that schematically shows details of the connections of optical transceiver cell 90 to an optical bus 150 in an integrated optical transceiver array, in accordance with an alternative embodiment of the invention. In this embodiment, bus 150 comprises a Tx waveguide 152, to which transmit tap 144 is coupled, and a LO waveguide 154, to which LO tap 146 is coupled. This configuration may facilitate balancing the relative levels of optical power that are provided to Tx waveguide 98 and to LO waveguide 100.

Typically, the optical radiation conveyed from bus 96 to waveguides 98 and 100 and then transmitted via the optical transducer is polarized, for example with a TE polarization. The optical radiation reflected from the target typically has both of the orthogonal TE and TM polarization components. In the preceding embodiments, however, only one of the received polarization components is coupled to receiver 114 by the optical transducer and coupler.

FIG. 8 is a block diagram that schematically illustrates an integrated optical transceiver cell 160 comprising a dual-port optical transducer 162, in accordance with an embodiment of the invention. For example, optical transducer 162 may comprise a grating coupler comprising two gratings, one of which couples radiation from a first waveguide 166 toward the target, while the other grating couples incoming radiation from the target into a second waveguide 168. Alternatively, one of the gratings may couple radiation of a first polarization, such as the TE polarization, from and to waveguide 166, while the other grating couples radiation of the orthogonal (TM) polarization into waveguide 168. (Alternatively, the roles of the TE and TM polarizations may be reversed.) Examples of grating couplers with these capabilities are shown in FIGS. 13-16.

Assuming transducer 162 to be a dual-polarization transducer, a 2×2 coupler 164 conveys outgoing TE radiation from Tx waveguide 98 to waveguide 166 for transmission via optical transducer 162 toward the target, and conveys incoming TE radiation from TE waveguide 166 to Rx waveguide 110 for input to receiver 114. Optical transducer 162 converts incoming TM radiation to TE and couples it into waveguide 168. Coupler 164 then couples the TE radiation in waveguides 166 and 168 into Rx waveguide 110. Thus, transceiver cell 160 achieves enhanced efficiency in collecting radiation reflected from the target, since both polarizations are received and detected.

Figure 10:
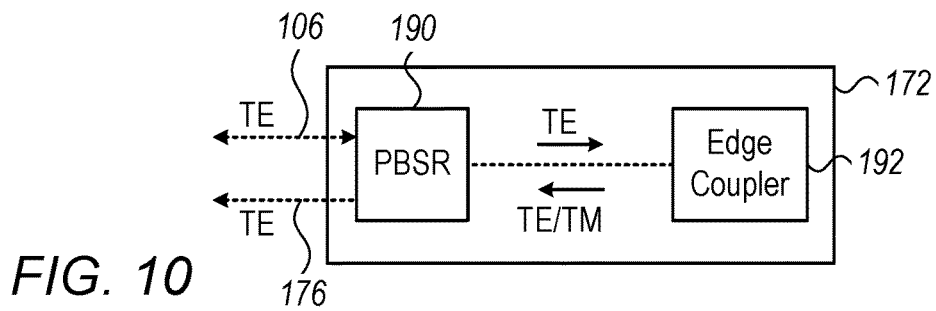
FIG. 10 is a block diagram that schematically shows details of an optical transducer, in accordance with an embodiment of the invention.

FIG. 9 is a block diagram that schematically illustrates an integrated optical transceiver cell 170 with a dual-polarization optical transducer 172, in accordance with an alternative embodiment of the invention. Optical transducer 172 may comprise, for example, an edge coupler with an integrated polarization beamsplitter rotator (PBSR), as shown in FIG. 10. Bidirectional waveguide 106 conveys outgoing TE radiation (for example) from coupler 104 to optical transducer 172 and also receives incoming TE radiation from the optical transducer. Coupler 164 passes this incoming TE radiation to a first receiver 174. Optical transducer 172 splits off the incoming TM radiation received from the target, rotates the polarization to TE, and passes this TE radiation via an input waveguide 174 to a second receiver 178.

Transceiver cell 170 in this embodiment is served by a transmit bus 180 and by a separate LO bus 182, for example as in system 50 (FIG. 2). A splitter 184 splits the LO beam received by LO waveguide 100 between receivers 174 and 178. Each receiver 174, 178 comprises a respective mixer, for example as shown in FIG. 4 or FIG. 5, for mixing and detecting the received radiation of the respective polarization. This arrangement enhances the detection efficiency of optical transceiver cell 170 relative to designs that capture incoming radiation of only a single polarization or that use a single receiver to detect radiation of both polarizations.

Figure 17:
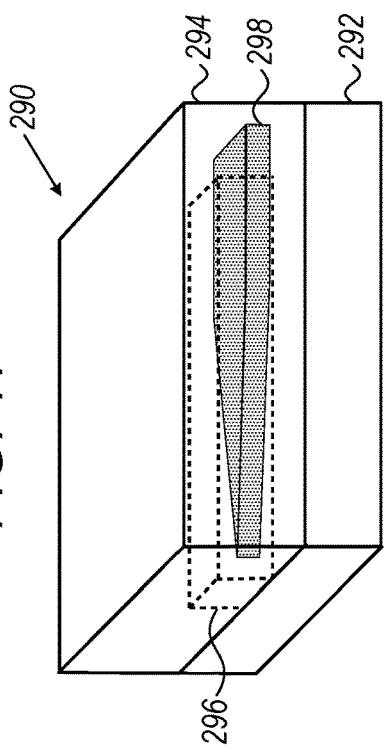
FIG. 17 is a schematic pictorial view of an optical edge coupler, in accordance with a further embodiment of the invention.

FIG. 10 is a block diagram that schematically shows details of optical transducer 172, in accordance with an embodiment of the invention. Transducer 172 comprises a PBSR 190, which passes TE radiation while splitting off and rotating the polarization of TM radiation. Thus, PBSR 190 passes outgoing TE radiation from waveguide 106 through to an edge coupler 192 for transmission toward the target and also passes incoming TE radiation back through waveguide 106. PBSR 190 rotates incoming TM radiation received by edge coupler 192 and couples this radiation into waveguide 176. An example of the physical structure of optical transducer 172 is shown in FIG. 17.

Alternatively, optical transducer 172 may be configured to receive and transmit TM radiation and to rotate the incoming TE radiation.

Figure 11:
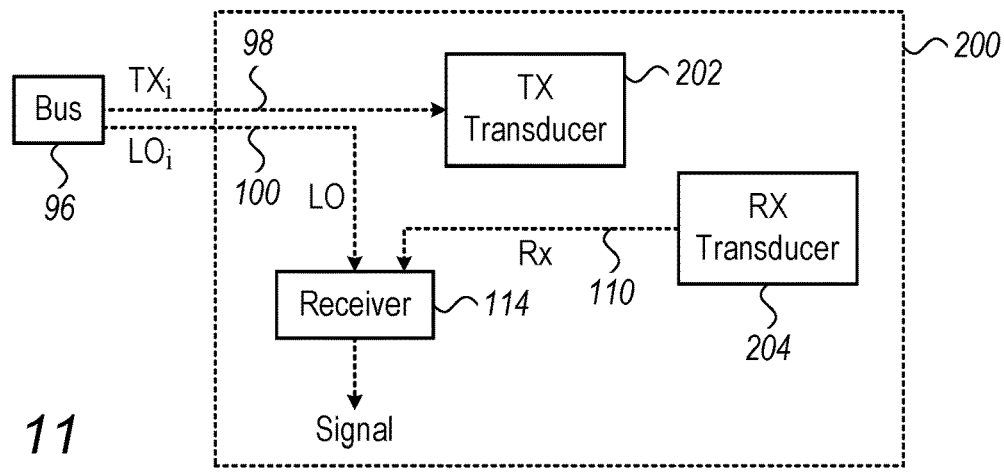
FIG. 11 is a block diagram that schematically illustrates an integrated optical transceiver cell, in accordance with an embodiment of the invention.

FIG. 11 is a block diagram that schematically illustrates an integrated optical transceiver cell 200, in accordance with another embodiment of the invention. In contrast to the preceding embodiments, in which the transceiver cells are designed for monostatic operation (with the transmitted and received beams sharing the same optical axis), optical transceiver cell 200 is configured for bistatic operation, with a certain displacement between the transmit and receive axes.

Thus, the optical transducer of cell 200 comprises a Tx transducer element 202, which couples coherent radiation from transmit waveguide 98 out toward the target; and a RX transducer element 204, which coupled incident optical radiation into receive waveguide 110. Transducer elements 202 and 204 may comprise grating couplers, for example, or separate edge couplers. The bistatic arrangement of cell 200 is advantageous in increasing the efficiency of transmission and reception, since there is no energy lost in coupling between the transmit and receive radiation paths. This arrangement requires additional external optics (not shown) to establish a suitable overlap of the fields of view of Tx and Rx transducer elements 202 and 204.

Figure 12:
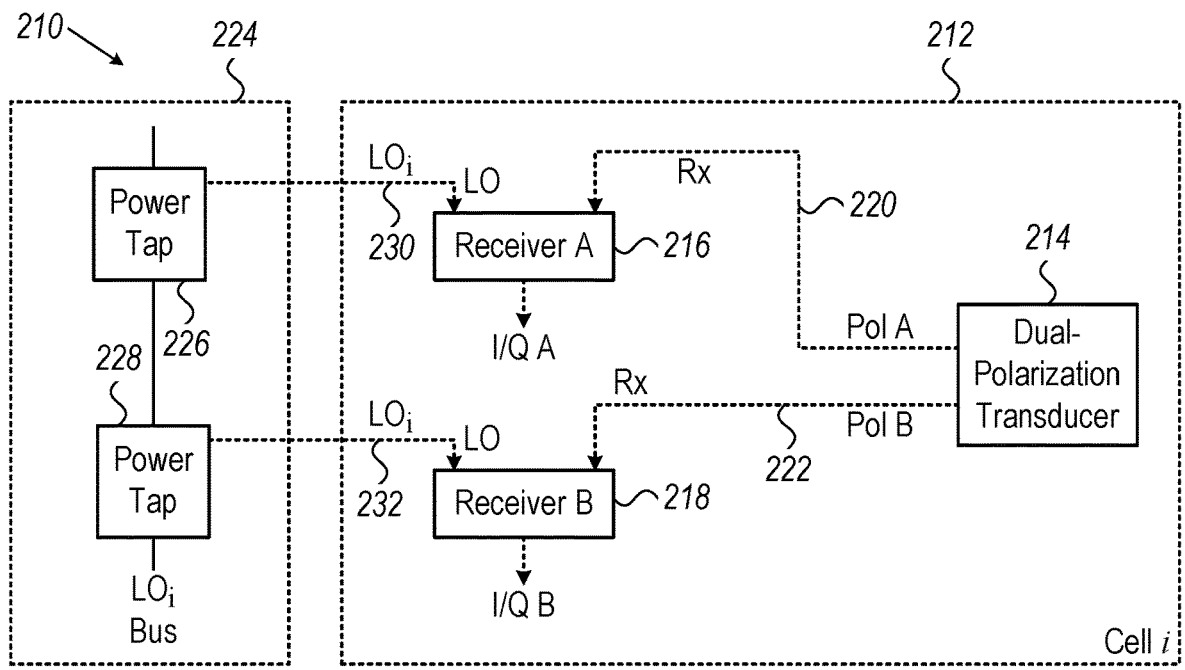
FIG. 12 is a block diagram that schematically shows details of an integrated optical receiver array, in accordance with another embodiment of the invention.

FIG. 12 is a block diagram that schematically shows details of an integrated optical receiver array 210, in accordance with another embodiment of the invention. In contrast to the preceding embodiments, array 210 comprises receiver cells 212, which sense radiation reflected from the target. Coherent radiation is transmitted toward the target through other channels (not shown). Receiver cell 212 comprises a dual-polarization optical transducer 214, as described above, which receives and conveys radiation of one polarization to a first receiver 216 and of the other, orthogonal polarization to a second receiver 218, via respective waveguides 220 and 222. A LO bus 224 distributes LO beams to receivers 216 and 218 via respective taps 226, 228 and LO waveguides 230 and 232. Receivers 216 and 218 mix the received and local beams and generate resulting electrical signals, which are marked I/Q A and I/Q B in FIG. 12.

Although the figures described above show certain particular configurations of optical transceiver cells, with particular arrangements of optical and photonic components, the scope of the present invention is by no means limited to these configurations. Rather, other combinations of the principles and components of the various embodiments that are described above will be apparent to those skilled in the art after reading the present disclosure. All such alternative implementations are considered to be within the scope of the present invention.

Optical Transducer Designs

The term "optical transducer," as used in the present description and in the claims, refers to a component or device that couples optical radiation between one medium and another. The optical transducers described herein perform the functions of coupling optical radiation from a waveguide to free space and vice versa. As further examples, these and other types of optical transducers can be used to couple optical radiation between a waveguide on a PIC and an optical fiber, or between waveguides and biological tissues.

Figure 13:
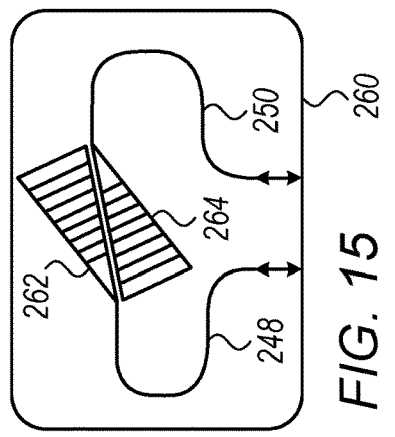
FIGS. 13, 14 and 15 are schematic top views of optical grating couplers, in accordance with embodiments of the invention.

FIG. 13 is a schematic top view of an optical grating coupler 231, in accordance with an embodiment of the invention. Coupler 231 can serve as the optical transducer in the transceiver cells described above, and particularly in the embodiments that include dual-port or dual-polarization transducers.

Optical grating coupler 231 comprises two gratings 233 and 234, which are oriented perpendicular to one another and are coupled to respective waveguides 236 and 238. The two gratings 233, 234 may be fabricated in separate layers on the substrate of the transceiver arrays, with one layer overlying the other, for example in patterned SiN and/or Si layers; or they may be fabricated as a single structure comprising both gratings in a single layer. Because of their geometrical orientations, gratings 233 and 234 couple optical radiation of two orthogonal polarizations between the free space above the transceiver cell and the respective waveguides 236 and 238. Because of the orthogonal geometrical relationship between gratings 233, 234 and the respective waveguides 236, 238, however, the optical radiation coupled by the gratings into both waveguides will have TE polarization within the waveguides.

Figure 14:
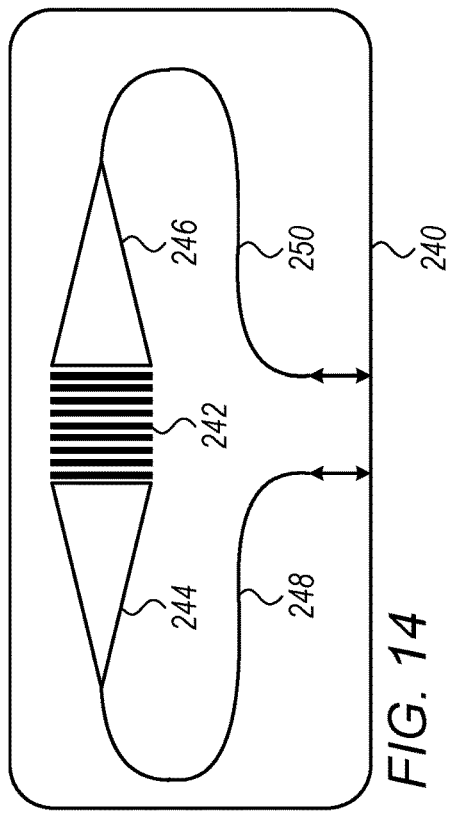

FIG. 14 is a schematic top view of an optical grating coupler 240, in accordance with another embodiment of the invention, which can similarly serve as the optical transducer in some of the transceiver cells described above. Coupler 240 comprises a grating 242 with two input/output ports 244, 246, which are connected to respective waveguides 248, 250. This dual-port configuration can be useful in increasing the level of power transmitted out of and into coupler 240, while potentially obviating the need for a beamsplitter between the transmit and receive arms of the transceiver cell. Alternatively, both waveguides 248 and 250 can be coupled together to transmit and/or receive the same beam.

Figure 15:
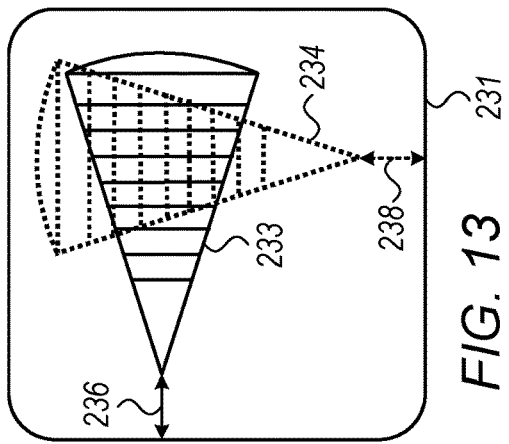

FIG. 15 is a schematic top view of an optical grating coupler 260, in accordance with an alternative embodiment of the invention. Optical gating coupler 260 is a two-port coupler, similar in operation to optical grating coupler 240 (FIG. 14). The side-by-side geometrical arrangement of gratings 262, 264 in coupler 260, however, is advantageous in enabling the gratings to be packed more tightly together on the substrate, and thus may be useful in reducing the sizes of the transceiver cells. In an alternative embodiment, one of gratings 262 and 264 can be used to transmit while other is used to receive light. The tight packing ensures that the received light couples into the receive grating even though the gratings occupy nominally different physical spaces.

Figure 16:
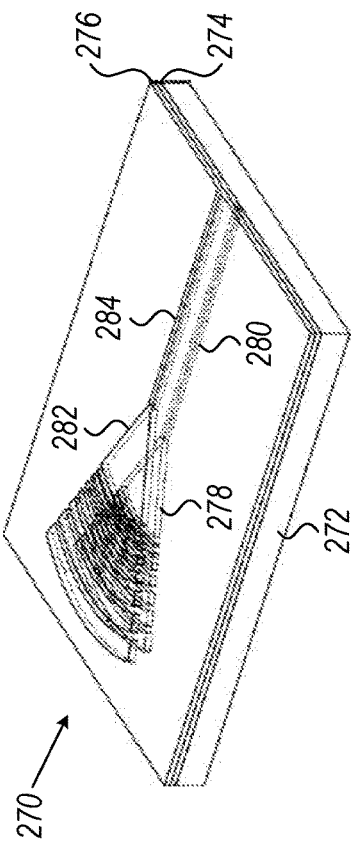
FIG. 16 is a schematic pictorial view of an optical grating coupler, in accordance with an embodiment of the invention.

FIG. 16 is a schematic pictorial view of a dual-port optical grating coupler 270, in accordance with an embodiment of the invention. Optical grating coupler 270 is formed on a PIC, which comprises a substrate 272, such as a SOI die, and successive waveguide layers 274, 276 deposited on the substrate. Waveguide layers 274, 276 may comprise silicon and SiN, for example, and are typically separated by dielectric ($SiO_2$) layers (shown in FIG. 18, for example). A first grating 278, along with a waveguide coupled to grating 278, is formed by etching layer 274. A dielectric layer is then deposited over grating 278, followed by waveguide layer 276. A second grating 282, overlying grating 278, is formed by etching layer 276, along with a waveguide 284 coupled to grating 282.

The structure and technique illustrated in FIG. 16 can be used, with appropriate orientation of the gratings and waveguides, in implementing a variety of dual-port optical transducer designs, such as the design shown in FIG. 13. Alternatively, this sort of design can be used in a split-aperture optical transducer, as described further hereinbelow with reference to FIGS. 18 and 19.

FIG. 17 is a schematic pictorial view of an optical edge coupler 290, in accordance with a further embodiment of the invention. This design can be used, for example, in implementing optical transducer 172 (FIG. 10). Edge coupler 290 is formed by patterning one or more waveguide layers 294, deposited on a PIC substrate 292. Waveguide layer 294 is patterned to define a waveguide 296, which terminates at the edge of the transceiver die in a spot-size converter 298. Converter 298 shapes the outgoing TE beam from the optical transducer to give the desired beam characteristics (such as spot size and numerical aperture), and also splits off and rotates the TM component of the incoming beam, following reflection from the target.

Figure 18:
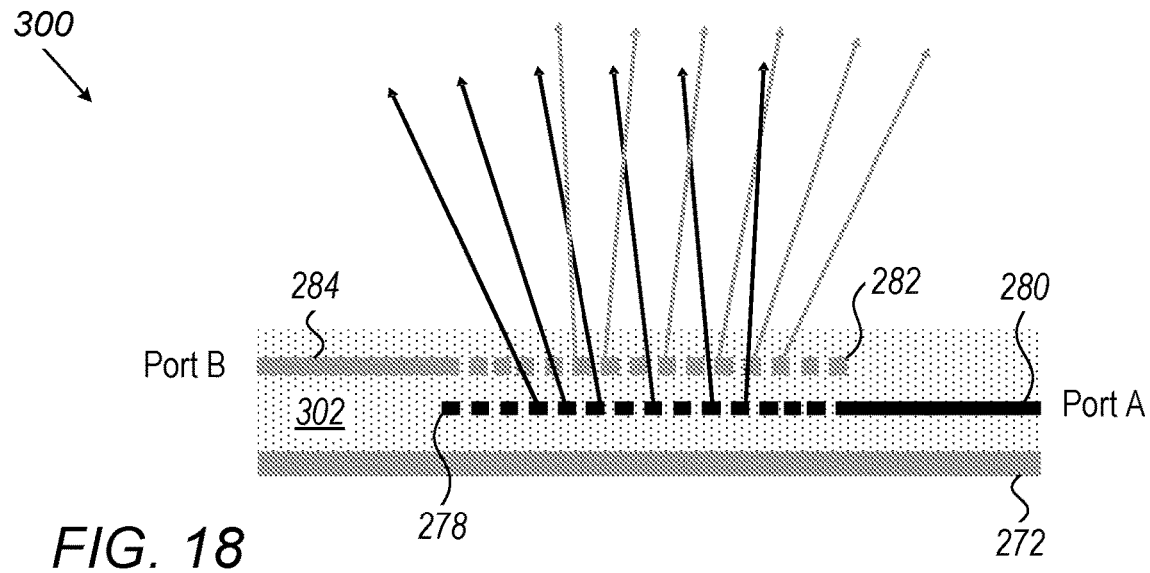
FIG. 18 is a schematic sectional view of an optical grating coupler, in accordance with an embodiment of the invention.

FIG. 18 is a schematic sectional view of an optical grating coupler 300, in accordance with an embodiment of the invention. Coupler 300 may be fabricated, for example, in the manner described above with reference to FIG. 16, and the same indicator numbers are therefore used in FIG. 18 to refer to the same components in the two figures. Gratings 278 and 282 are encapsulated in and separated by a dielectric 302, such as $SiO_2$.

In the present embodiment, waveguide 284 is assumed to be the transmit waveguide, while waveguide 280 is the receive waveguide. Grating 282 couples coherent radiation between the transmit waveguide and a first range of angles in a space over substrate 272. Grating 278 couples the optical radiation that is incident on grating coupler 300 within a second range of angles, different from the first range, into the receive waveguide. The two ranges of angles are disjoint in the far field of gratings 278 and 282. Thus, the transmitted and received beams share the same optical aperture but occupy different angular ranges within the aperture.

The design shown in FIG. 18 can enhance the efficiency of transmission and reception in a dual-port grating coupler. Alternatively, the principles of this sort of "split-aperture" design can be used in other sorts of coupling schemes, for example schemes involving transmission and/or reception of light of two different polarizations or two different wavelengths.

Figure 19:
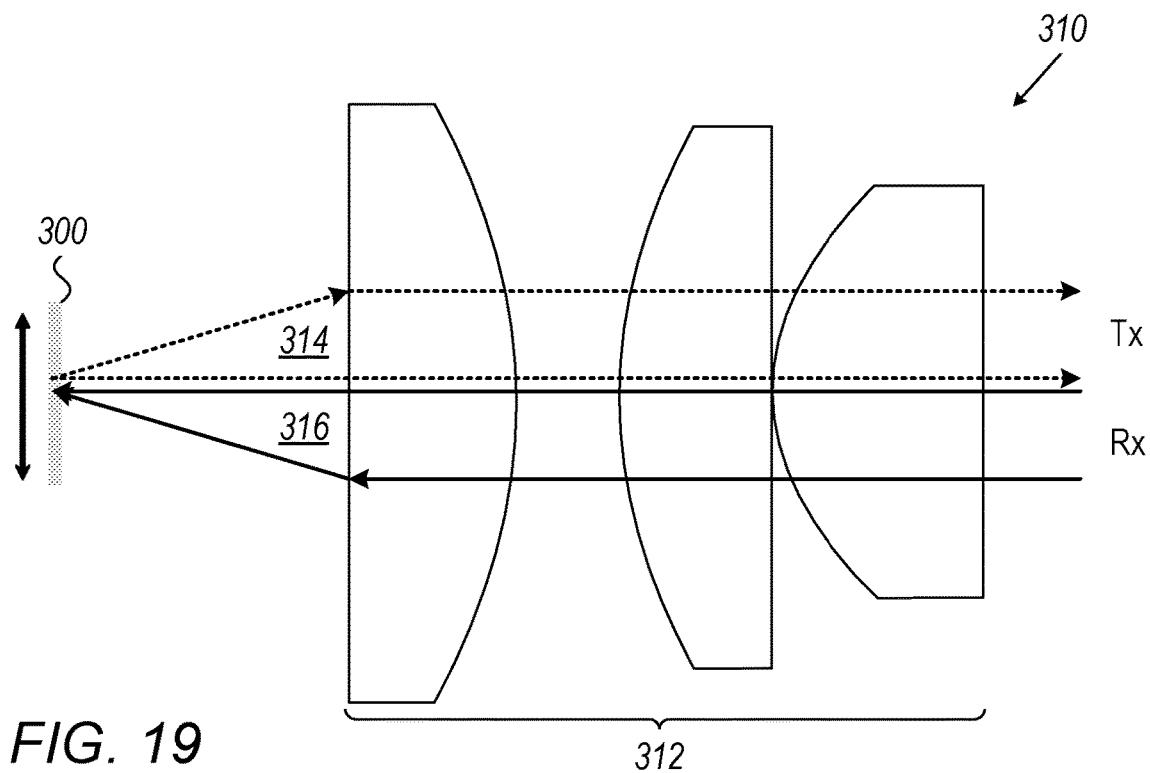
FIG. 19 is a schematic side view of an optical system with a split aperture, in accordance with an embodiment of the invention.

FIG. 19 is a schematic side view of an optical system 310 with a split aperture, in accordance with an embodiment of the invention. System comprises optical grating coupler 300, as described above, along with optics 312 mounted over the substrate of the optical grating coupler, for example collimating optics. The outgoing (Tx) beam from grating 282 is coupled into an angular range 314, while the incoming radiation is coupled from an angular range 316 into grating 278.

Array and Scanner Configurations

Current PIC technologies are limited in terms of the number and density of sensing cells that can be fabricated on a chip of reasonable size. Therefore, at any given angle of scanner 46 (FIG. 1), the optical apertures and corresponding fields of view of the sensing cells may not cover the target densely enough for the application. In other words, the sensing cells are physically sparse relative to the desired density of coverage of the target. In the embodiments that are described below, processor 48 collects signals from the sparse array of sensing cells at multiple different scan angles and combines them to map the target with the desired pixel density.

In some embodiments, the optical apertures of the sensing cells are disposed in a row, which has a row axis perpendicular to a scan direction of the scanner. The scanner sweeps the fields of view of the sensing cells across the target in order to create a full map of the desired density.

Additionally or alternatively, in some embodiments the optical apertures of the cells are located at respective nodes on respective rows and columns of a two-dimensional rectangular grid, such that only a minority of the nodes on the respective rows and columns are occupied by the optical transducers. In other words, the optical apertures are distributed sparsely, occupying only a subset of the nodes of the grid. The scanner scans the optical apertures of the sensing cells across the target along the rows of the grid so that each of the optical apertures is projected successively onto a respective sequence of multiple nodes in the rectangular grid on the target. In some embodiments, the scanner also scans the optical apertures along the columns of the grid. In this manner, the processor is able to scan the optical apertures over all the desired points in the grid, with a density determined by the scan parameters.

Figure 20A:
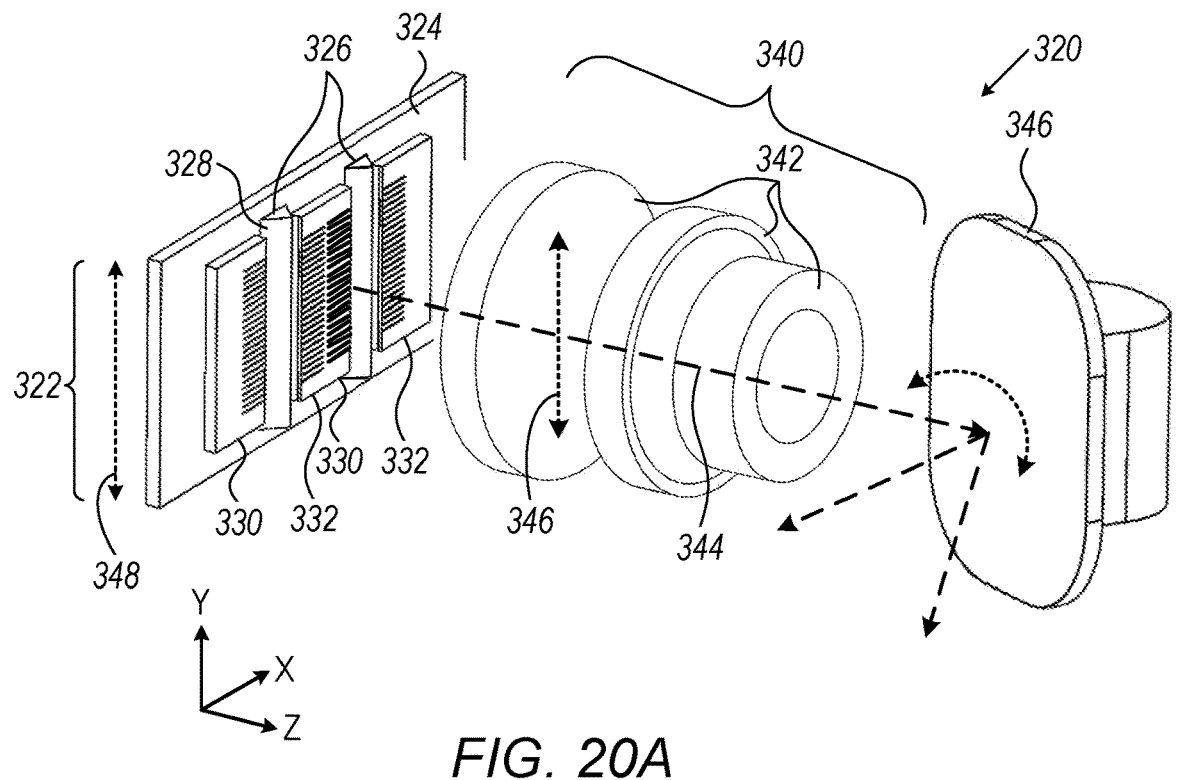
FIG. 20A is a schematic pictorial view of an optical sensing system, in accordance with an embodiment of the invention.
Figure 20B:
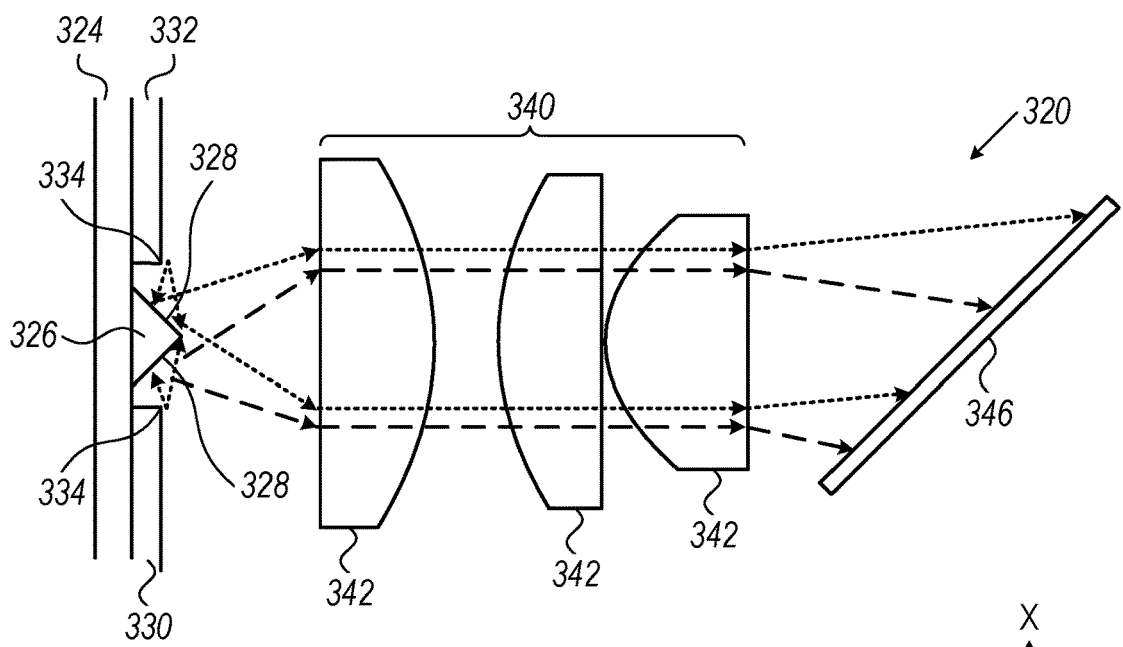
FIG. 20B is a schematic sectional view of the optical sensing system of FIG. 20A.
Figure 20C:
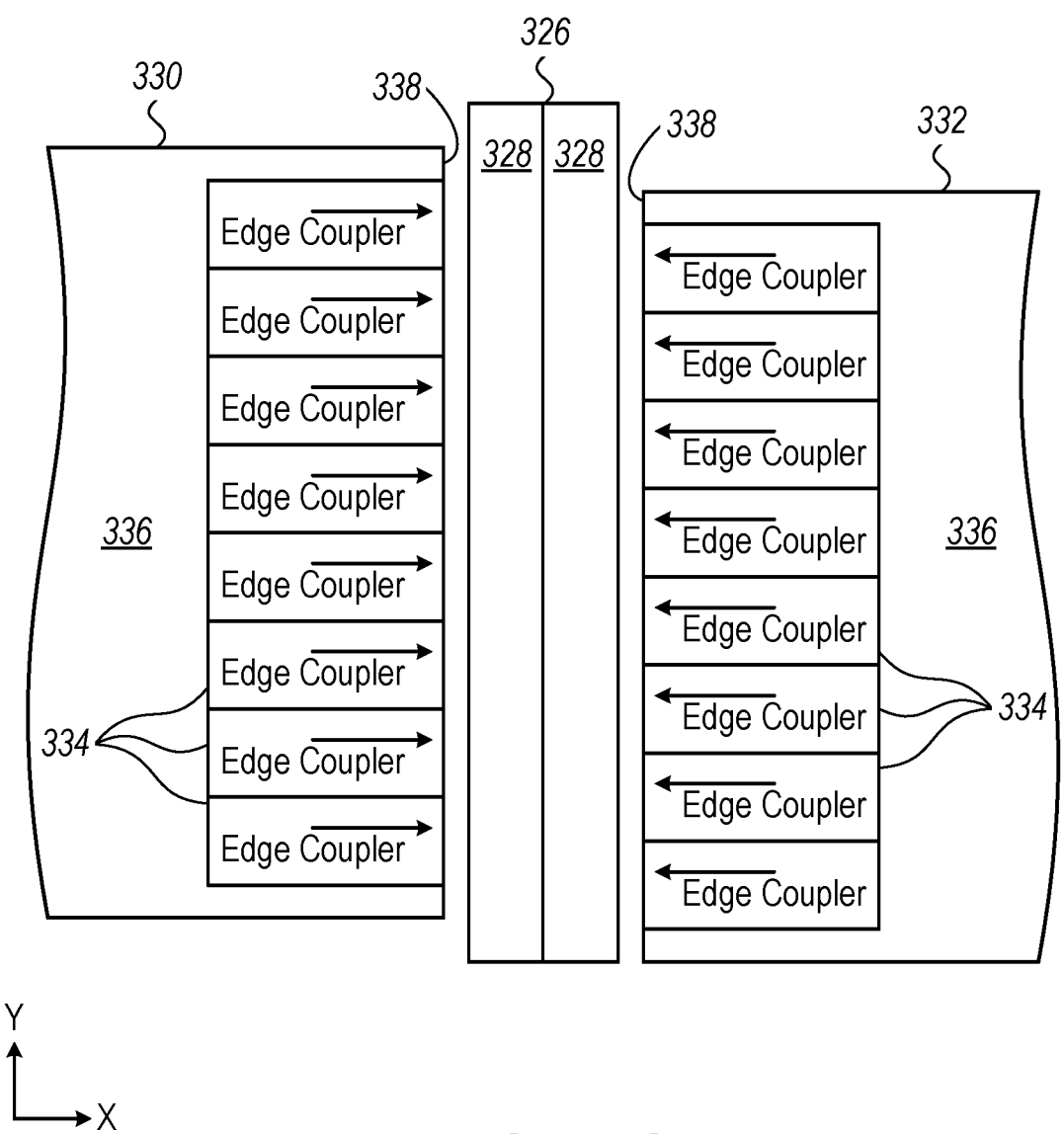
FIG. 20C is a schematic frontal view showing details of a coupling arrangement used in an optical sensing system, in accordance with an embodiment of the invention.

Reference is now made to FIGS. 20A, 20B and 20C, which schematically illustrate an optical sensing system 320, in accordance with an embodiment of the invention. FIG. 20A is a pictorial view of optical sensing system 320, while FIG. 20B is a sectional view of the optical sensing system. FIG. 20C is a schematic frontal view showing details of a coupling arrangement used in optical sensing system 320.

System 320 comprises a sensing subassembly 322, comprising a carrier substrate 324, with one or more dual folding mirrors 326 mounted on the carrier substrate. Dual folding mirror 326 comprises a pair of reflecting surfaces 328 disposed at opposite angles relative to a normal to carrier substrate 324. In the pictured embodiments, dual folding mirror 326 has a triangular profile, with reflecting surfaces 328 oriented respectively at +45° and −45° relative to the normal, which is parallel to the Z-axis in the coordinate system shown in the figure. The advantages of this configuration are explained below. Alternatively, other sorts of folding mirrors may be used. Although subassembly 322 is shown in FIG. 20A to comprise two dual folding mirrors 326 with associated sensing devices 330, 332, in alternative embodiments, the sensing subassembly may comprise only a single dual folding mirror and associated sensing devices; or it may comprise three or more dual folding mirrors and sensing devices.

Sensing subassembly 322 comprises a pair of sensing devices 330 and 332 mounted on carrier substrate 324 on opposing sides of dual folding mirror 326. Each sensing device 330, 332 comprises a planar device substrate 336, which is mounted on carrier substrate 324 such that an edge of device substrate 336 is in proximity to a corresponding reflecting surface 328 of dual folding mirror 326. Each sensing device 330, 332 comprises a respective array of sensing cells formed on the corresponding device substrate 336, for example as illustrated in FIGS. 1 and 2 or in FIG. 22, as described below. The sensing cells typically comprise transceiver cells, as shown in the preceding figures, or possibly receiver cells, for example as shown in FIG. 12.

The sensing cells in devices 330 and 332 comprise optical transducers in the form of respective edge couplers 334, which are arrayed along an edge 338 of device substrate 336 so as to couple optical radiation between the cells and the proximate reflecting surface 328. Edges 338 are both parallel to the Y-axis, as is the longitudinal axis of dual folding mirror 326. Edge couplers 334 have a certain pitch, i.e., the center-to-center distance between adjacent edge couplers along the Y-axis, which is limited by the constraints of the PIC technology that is used to produce devices 330 and 332. To increase the scan density, edge couplers 334 can be staggered, i.e., edge couplers 334 in device 332 can be offset along the Y-axis by half the pitch relative to edge couplers 334 in device 330, as shown in FIG. 20C. A scan pattern that takes advantage of this staggering is illustrated in FIG. 21.

Edge couplers 334 define the respective optical apertures of the sensing cells in the arrays on devices 330 and 332. Imaging optics 340, comprising one or more optical elements 342, image these optical apertures along an optical axis 344 onto the target, thus defining the respective field of view of each sensing cell. A scanner scans the fields of view of the sensing elements across the target. In the embodiment shown in FIG. 20A, the scanner comprises a rotating mirror 346, which is disposed between dual folding mirror 326 and the target and scans the imaged optical apertures across the target. Rotating mirror 346 may comprise, for example, a single- or dual-axis galvanometer or MEMS (microelectromechanical systems) mirror assembly or a rotating polygonal mirror. Alternatively, other sorts of scanners, such as Risley prisms, may be used.

Additionally or alternatively, the scanner in system 320 may operate by shifting at least one of optical elements 342 and/or shifting carrier substrate 324 in a direction transverse to optical axis 344. The shift of one of optical elements 342 is represented in FIG. 20A by an arrow 346, while the shift of carrier substrate 324 is represented by an arrow 348. Both shifts are parallel to the Y-axis in the pictured embodiment, and will accordingly shift the fields of view of the sensing cells in the Y-direction, while rotating mirror 346 scans the fields of view of the sensing cells along the X-axis.

Figure 24:
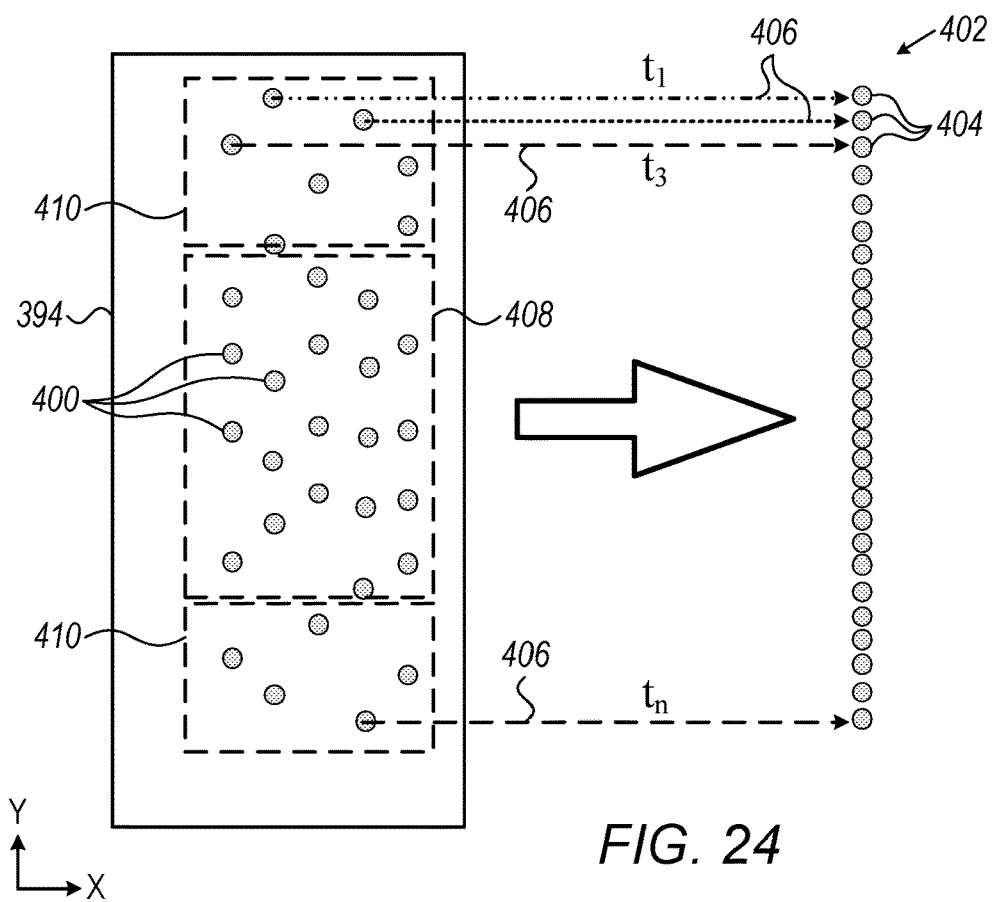
FIG. 24 is a schematic frontal view of an optical transceiver array and a scan pattern created by the array, in accordance with an embodiment of the invention.

FIG. 21 is a schematic frontal view of a target 350 irradiated by optical sensing system 320 over a sequence of scan times, in accordance with an embodiment of the invention. An initial scan pattern 352 (at time $t_{0,0}$) represents the geometry of the fields of view of the sensing cells in devices 330 and 332, which correspond to respective optical apertures 354 of edge couplers 334, on opposing sides of dual folding mirror 326. Optical apertures 354 are disposed on respective rows 356 and columns 358 of a rectangular grid, in the staggered configuration described above due to the offsets between edge couplers 334 on the opposing sides of mirror 326. As noted earlier, imaging optics 340 form an image of the rectangular grid on target 350. In scan pattern 352, half the nodes of the rectangular grid are occupied by optical apertures 354. In other embodiments (for example as shown in FIG. 24), the coverage of the rectangular grid may be even sparser, with optical apertures at only a minority of the nodes of the rectangular grid.

A scanner, such as rotating mirror 346, scans optical apertures 354 across target along rows 356 of the grid so that the optical apertures are projected successively onto respective sequences of multiple nodes in the rectangular grid on the target. In the present embodiment, mirror 346 scans optical apertures 354 only along rows 356, while either substrate 324 or optical element 342 is shifted to scan the optical elements along columns 358. Alternatively, as noted above, mirror 346 may scan the optical apertures along both the row and column directions. Further alternatively, for some applications, a one-dimensional scan, along either the rows or the columns, may be sufficient. As yet another alternative, a scanner may implement other sorts of scan patterns, not necessarily scanning along rows 356 or columns 358.

In the scan pattern shown in FIG. 21, mirror 346 scans optical apertures 354 along rows 356, in the X-direction, thus adding successive scan points 366 along the corresponding rows at successive times $t_{0,1}, t_{0,2}, \ldots, t_{0,n}$, represented in the figure by frames 360, 362, ..., 364. After the scans along these rows have been completed, substrate 324 or optical element 342 is shifted along the Y-axis, causing the images of optical apertures 354 on target 350 to shift accordingly. As mirror 346 scans back along the X-direction, additional scan points 368 are added along the next row of the grid, as illustrated in frames 370, 372, ..., at times $t_{1,1}, t_{1,2}$, etc. This process is repeated until target 350 is covered by scan points 366, 368, ..., to the desired density.

In FIG. 21, target 350 is scanned at a uniform speed and scan density. In alternative embodiments, a scanner (such as rotating mirror 346 and/or motion of substrate 324 or optical element 342) may be configured to vary the speed of scanning the optical apertures over different areas of the target and/or to vary the density of the nodes of the grid onto which the optical apertures are projected over different areas of the target. Additionally or alternatively, a controller, such as processor 48, may actuate the sensing cells of devices 330 and 332 selectively as the optical apertures are scanned across the target so as to vary the density of the nodes of the grid onto which the optical apertures are projected over different areas of the target. An implementation of these principles is shown, for example, in FIGS. 34-36.

Figure 22:
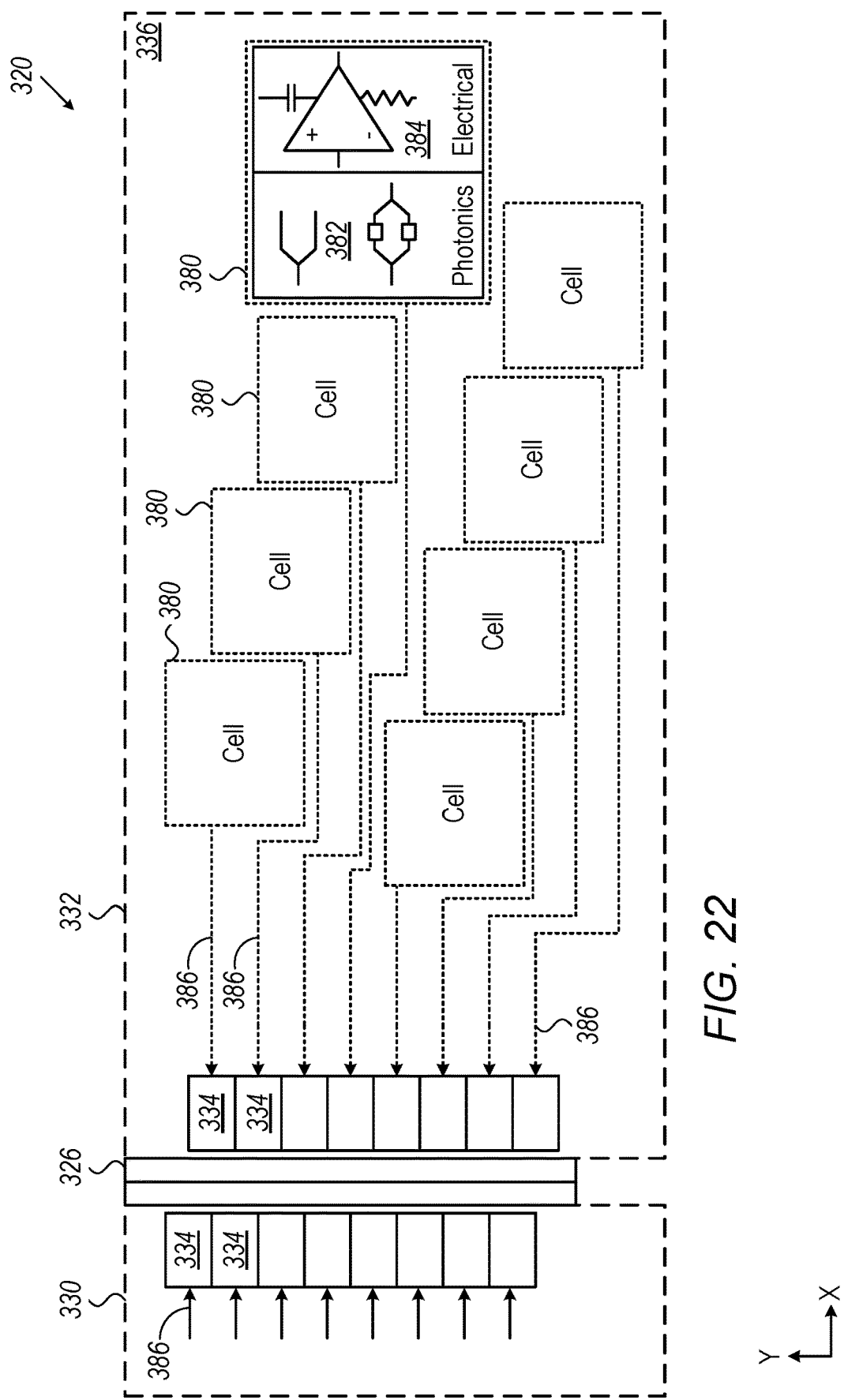
FIG. 22 is a schematic frontal view of an optical transceiver array and an associated coupling arrangement used in an optical sensing system, in accordance with an embodiment of the invention.

FIG. 22 is a schematic frontal view of sensing device 332 in system 320, in accordance with an embodiment of the invention. Device 332 (and similarly device 330) can be seen in this embodiment to comprise an array of optical transceiver cells 380, which are coupled to respective edge couplers 334 by waveguides 386 disposed on device substrate 336. Each transceiver cell 380 comprises respective photonic components 382 and electrical components 384, as in the various transceiver cells that were shown and described above. Consequently, the respective widths of cells 380 (in the Y-direction) is greater than the desired pitch of edge couplers 334. To avoid having to increase this pitch, photonic components 382 and electrical components 384 of cells 380 are disposed at different, respective distances from the edge of substrate 336 where edge couplers 334 are formed, as illustrated in FIG. 22. Waveguides 386 of different lengths connect the edge couplers to the photonic components of the respective cells.

The design and functionality of cells 380 may incorporate suitable features and components from any of the embodiments that were shown and described above. Thus, cells 380 typically comprise both transmit waveguides, for directing coherent radiation through edge couplers 334 toward dual folding mirror 326 for projection onto the target, and receive and LO waveguides, for receiving the reflected optical radiation and mixing it with a part of the outgoing coherent radiation. As in the preceding embodiments, a detector, such as a balanced photodiode pair, in each cell 380 detects the mixed radiation and outputs a corresponding electrical signal. (Alternatively, as in the embodiment of FIG. 12, for example, cells 380 may be configured only for receiving, mixing, and detecting the received radiation, without transmission functions.)

Additionally or alternatively, as in the embodiments described above, devices 330 and 332 may comprises respective optical buses for conveying coherent radiation to cells 380, and transceiver cells 380 may comprise taps coupled to extract a portion of the coherent radiation propagating through the optical buses for transmission toward the target and mixing with the received optical radiation.

Further alternatively, systems and methods for scanned coherent sensing as described herein may be implemented using sensing cells of other sorts, as will be apparent to those skilled in the art after reading the present description. Additionally or alternatively, such systems and methods can be used to project images, in addition to or instead of the sensing applications described above.

Figure 23:
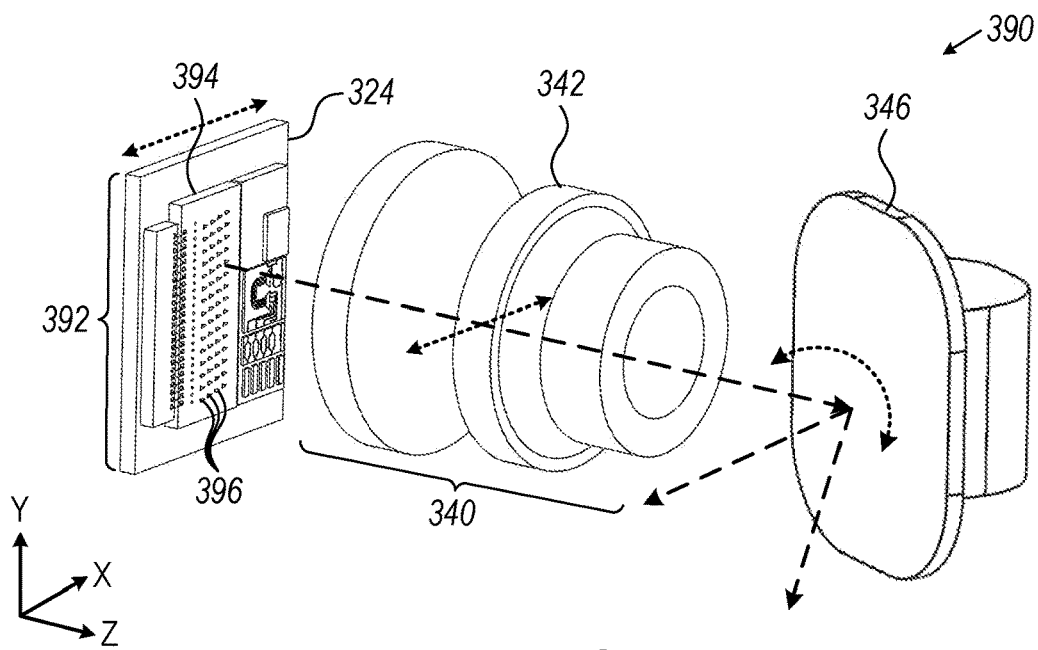
FIG. 23 is a schematic pictorial view of an optical sensing system, in accordance with another embodiment of the invention.

FIG. 23 is a schematic pictorial view of an optical sensing system 390, in accordance with another embodiment of the invention. System 390 comprises a sensing subassembly 392, which comprises a sensing device 394 mounted on carrier substrate 324. Sensing device 394 comprises an array of transceiver cells, with respective optical transducers arranged in a sparse two-dimensional pattern along the rows and columns of a rectangular grid. The optical transducers in this embodiment, may comprise, for example, grating couplers, as shown and described above. Each such optical transducer defines the optical aperture of the corresponding transceiver cell.

In the two-dimensional arrangement of the optical transducers in device 394, there is at least one optical transducer positioned on each row of the rectangular grid of scan points that is to cover the target. Therefore, it may be sufficient in the present embodiment to scan the optical apertures of the transceiver cells in a single direction, i.e., in the X-direction as shown in FIG. 23. This scan may be accomplished, for example, by rotating mirror 346 or by shifting either substrate 324 or one of optical elements 342 transversely, or by a combination of these or other means.

FIG. 24 is a schematic frontal view of optical apertures 400 of an optical transceiver array in sensing device 394, along with a single column 402 of a scan pattern created by the array, in accordance with an embodiment of the invention. The entire scan pattern comprises multiple columns 402 of this sort, each column comprising multiple scan points 404.

As optical apertures 400 are scanned in the X-direction across the target, each aperture describes a corresponding horizontal path 406 across the target. Each column 402 contains a respective point 404 on each path 406. The pitch of points 404 is determined by the vertical (Y) spacing of optical apertures 400; but because the apertures are spread apart in the horizontal (X) direction, the pitch may be much smaller than the actual widths of the transceiver cells in device 394. Because optical apertures 400 are spread apart in the horizontal direction, scan points 404 in any given column 402 will be traversed at different times during the scan, marked $t_1, \ldots, t_n$ in FIG. 24. Processor 48 uses the known geometry of the array and the known scan speed in assembling the data points acquired at different times from different transceiver cells into the proper geometrical columns 402.

In some embodiments, system 390 may be configured to scan the target non-uniformly. As one example, mirror 346 may sweep across different areas of the target at different speeds. As another example, optical apertures 400 may be distributed non-uniformly across the area of device 394. Thus, as shown in FIG. 24, optical apertures 400 are distributed more densely in a central zone 408 of the array than in peripheral zones 410. Consequently, the pitch of points 404 in column 402 will be finer in the central area of the scan than in the periphery. Additionally or alternatively, the pitch may be controlled dynamically by activating certain sensing cells and deactivating others.

FIGS. 25A, 25B and 25C are schematic frontal views of a target 420 irradiated by an optical sensing system over a sequence of scan times, in accordance with an embodiment of the invention. In this embodiment, the optical sensing device comprises a larger number of transceiver cells, each having its optical aperture 400 defined by a respective optical transducer. These transducers may comprise, for example, grating couplers or edge couplers with corresponding turning mirrors, or any other suitable type of vertical couplers. As in the preceding embodiment, the vertical (Y) pitch of the scan pattern is defined by the vertical offset between optical apertures 400 at different nodes of the rectangular grid. The pattern of nodes repeats four times over the horizontal (X) width of the array, with a period indicated by an arrow 422. The large number of transceiver cells and the repeating pattern enable the system to cover a large area of the target with only a limited scan range, corresponding to the angular extent of the period of repetition indicated by arrow 422. In this and other embodiments described herein, the horizontal and vertical (X and Y) axes are defined as such arbitrarily for the sake of convenience and clarity and may be interchanged freely.

In an alternative embodiment (not shown in the figures), wavelength-based scanning may be used. For example, mirror 346 may be replaced by a dispersive element, such as a diffraction grating, and the radiation source may scan over a range of wavelengths. The dispersive element translates the varying wavelength into angular scanning, thus increasing the density of coverage of the target.

FIG. 25A represents the initial scan frame with the scanner (such as a mirror or shift of the device substrate or optics, or a wavelength scan with a dispersive element in place of mirror 346) in its starting position. In the next scan frame, shown in FIG. 25B, each optical aperture 400 is scanned horizontally by a single increment. These horizontal increments continue over the angular scan range until the entire target has been covered, as illustrated in FIG. 25C.

Pitch Enhancement Using Tilted Arrays

The embodiments described above provide techniques for achieving a fine scan pitch using PIC-based sensing arrays in which the optical apertures of the sensing device are arranged in a two-dimensional pattern. In some applications, however, linear arrays are used, for example due to limitations of size and cost. There is a need in such applications, as well, to reduce the scan pitch to an angular dimension that is smaller than the physical pitch of the sensing array.

Some embodiments of the present invention address this need by tilting the array of sensing cells relative to the rotational axis of the scan (or equivalently, tilting the rotational axis of the scan relative to the row of optical apertures of the sensing array). In these embodiments, the sensing device comprises at least one planar substrate with an array of sensing cells disposed on the substrate. The sensing cells comprise respective optical transducers arranged in a row, such as edge couplers along the edge of the substrate, which define respective optical apertures of the cells. The scanner comprises a mirror, which projects and scans the optical apertures across the target while rotating about a rotational axis that is oriented at an oblique angle relative to the row axis of the optical apertures.

This tilt between the rotational axis and the row axis effectively reduces the angular spacing between the optical apertures in the direction perpendicular to the scan direction, as illustrated in the figures that follow. This geometrical arrangement can also be applied in apparatus in which the sensing device comprises multiple planar substrates, with a respective row of the optical transducers disposed one each substrate.

Figure 26A:
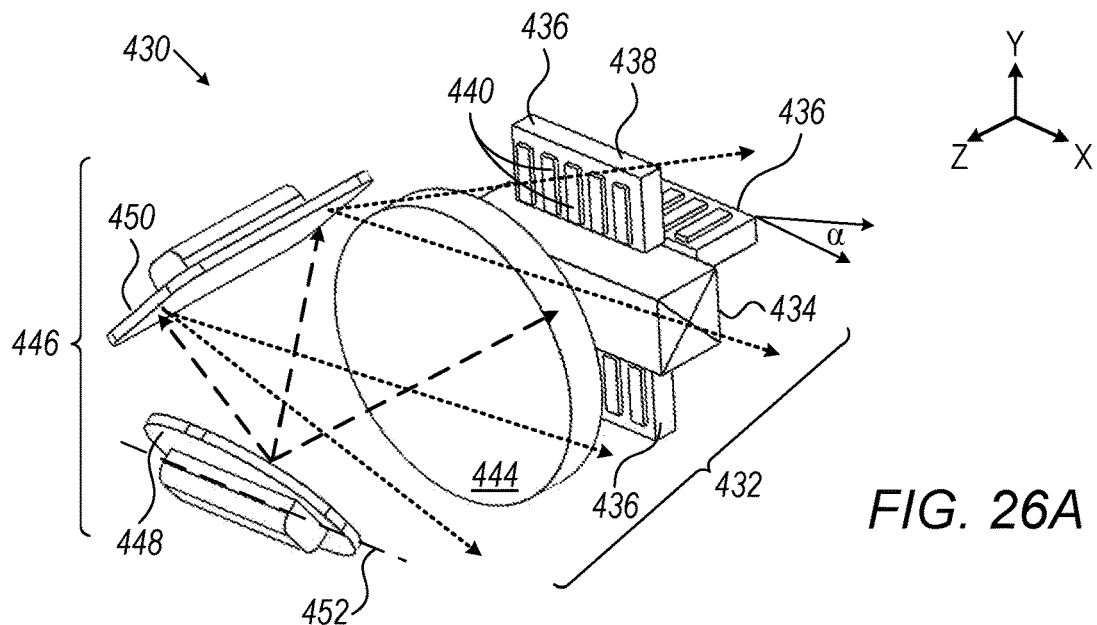
FIG. 26A is a schematic pictorial view of an optical sensing system, in accordance with yet another embodiment of the invention.
Figure 26B:
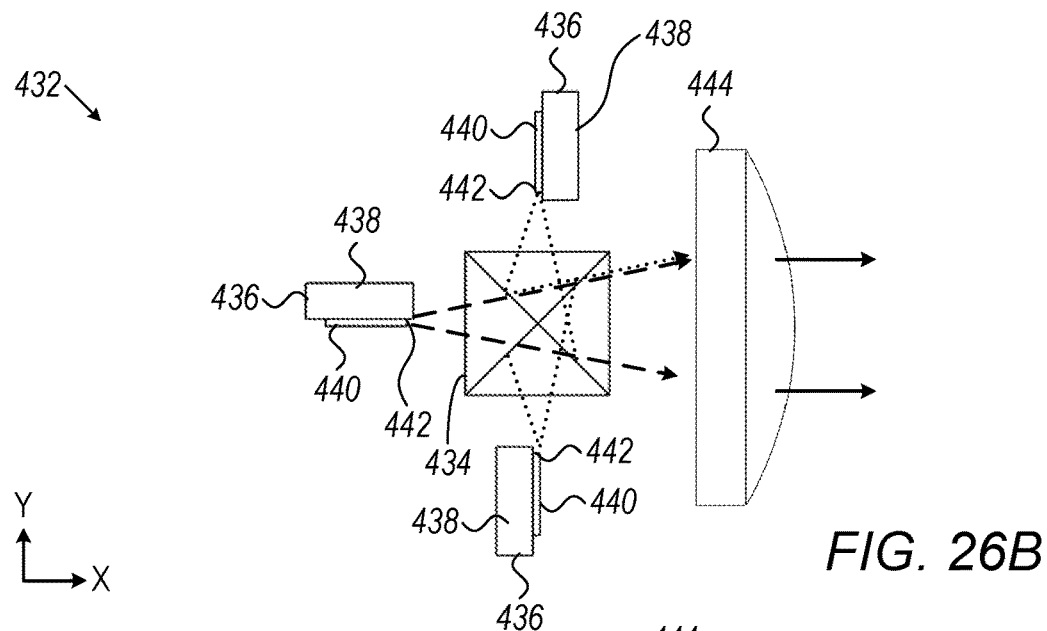
FIGS. 26B and 26C are schematic top and side views, respectively, of an optical module used in the optical sensing system of FIG. 26A, in accordance with an embodiment of the invention.
Figure 26C:
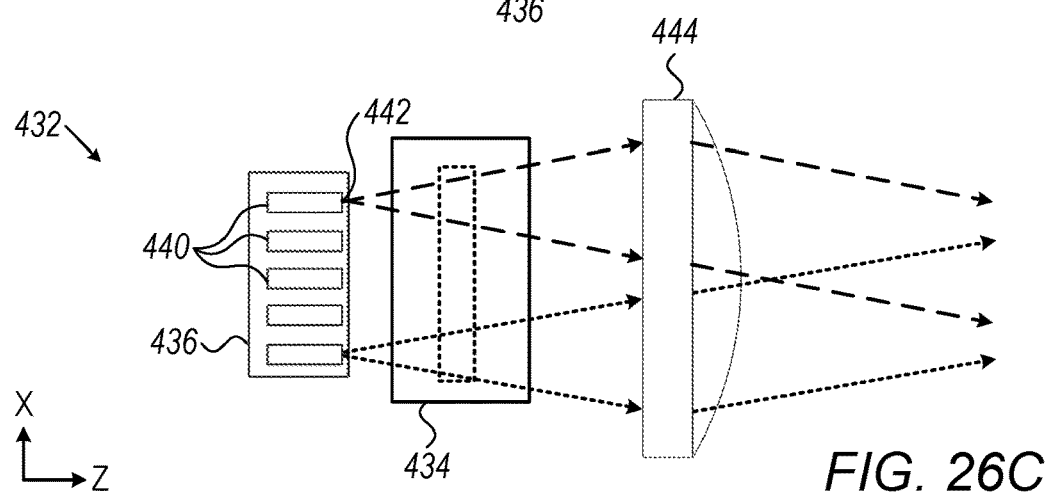

Reference is now made to FIGS. 26A, 26B and 26C, which schematically illustrate an optical sensing system 430, in accordance with an embodiment of the invention. FIG. 26A is a pictorial view of the system, while FIGS. 26B and 26C are schematic top and side views, respectively, of an optical module 432 used in system 430.

Optical module 432 comprises a beamsplitter cube 434, configured as an X-cube, as is known in the art. Three sensing devices 436 are fixed to respective faces of beamsplitter cube 434. This arrangement is useful, for example, in combining the fields of view of two or three sensing devices having different operating wavelength ranges, wherein the beamsplitter cube directs optical radiation in the respective wavelength range from and to each of the sensing devices. Alternatively, a beamsplitter cube may be used in combining the fields of view of two sensing devices that transmit and/or receive optical radiation of orthogonal polarizations.

Each sensing device 436 comprises a planar substrate 438 with a row of sensing cells 440, for example optical transceiver cells, as described above, formed on substrate 438. Each sensing cell 440 comprises a respective optical transducer 442, for example an edge coupler at the edge of substrate 438 that is adjacent to beamsplitter cube 434. Optical transducers 442 define respective optical apertures of sensing cells 440. The optical apertures in each sensing device 436 are arranged along a row axis that is parallel to the edge of substrate 438, i.e., parallel to the X-axis in the figures. Imaging optics 444 project the optical apertures onto a target.

A scanner 446 comprises a pair of rotating mirrors 448 and 450, which scan the projected optical apertures across the target in two dimensions. Mirror 448 rotates about a rotational axis 452 that is oriented at an oblique angle (a) relative to the row axes of the optical apertures. As a result of this tilt between the axes, the effective pitch of the optical apertures in the direction perpendicular to the scan is reduced.

Figure 27:
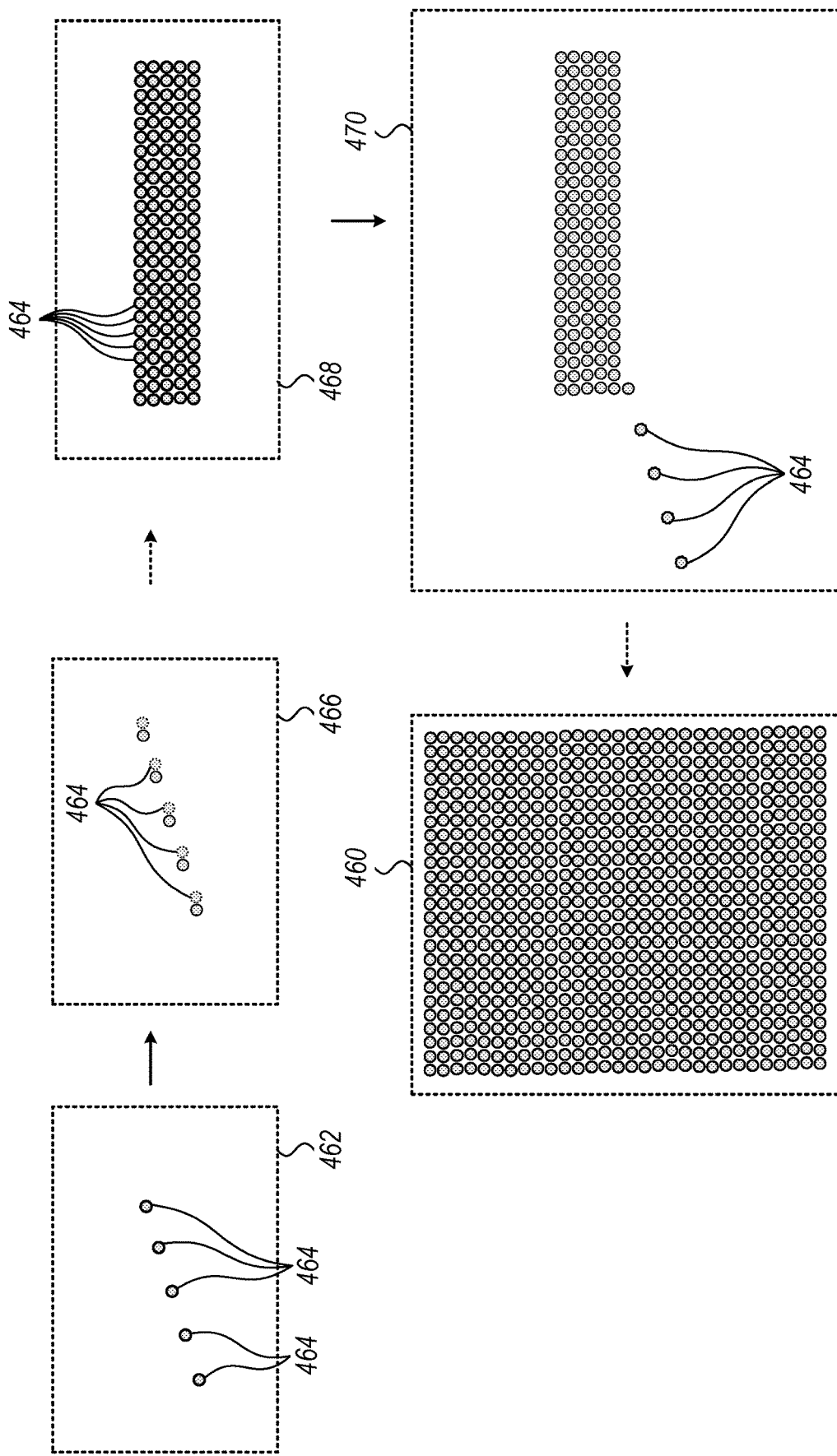
FIG. 27 is a schematic frontal view of a target irradiated by the optical sensing system of FIG. 26A over a sequence of scan times, in accordance with an embodiment of the invention.

FIG. 27 is a schematic frontal view of a target 460 irradiated by optical sensing system 430 (FIG. 26A) over a sequence of scan times, in accordance with an embodiment of the invention. An initial frame 462 shows a tilted row of scan points 464 corresponding to the projection of the boresighted optical apertures of transducers 442 onto the target. The tilt of the row of scan points corresponds to the tilt between the row axis and the rotational axis of mirror 448. This tilt give rise to a fine pitch between scan points 464 in the vertical direction. Frames 466, . . . , 468 show scan points 464 that are then acquired as scanner 446 sweeps the optical apertures horizontally across target 460.

After scanning the entire horizontal band covered by the projection of the optical apertures in frames 462 through 468, scanner 446 steps the optical apertures vertically and acquires scan points 464 across the next horizontal band, as shown in a frame 470. This process is repeated until the entire target 460 has been scanned to the desired resolution.

Reference is now made to FIGS. 28A, 28B and 28C, which schematically illustrate an optical sensing system 480, in accordance with yet another embodiment of the invention. FIG. 28A is a pictorial view of system 480, while FIGS. 28B and 28C are schematic top and side views, respectively, of an optical module 482 used in system 480. The principles of construction and operation of system 480 are similar to those of system 430, as shown and described above, and the same reference numbers are used to indicate the components of system 480 as were used to designate the corresponding components in system 430.

In contrast to system 430, however, planar substrates 438 of sensing devices 436 in optical module 482 are stacked along a direction (the Y-direction in FIGS. 28A-C) that is perpendicular to the rows of optical transducers 440. This arrangement enables system 480 to project multiple parallel rows of the optical apertures of sensing device 436 onto the target. As in the preceding embodiment, the row axes are tilted relative to rotational axis 452 of mirror 448 by an angle α.

Figure 29:
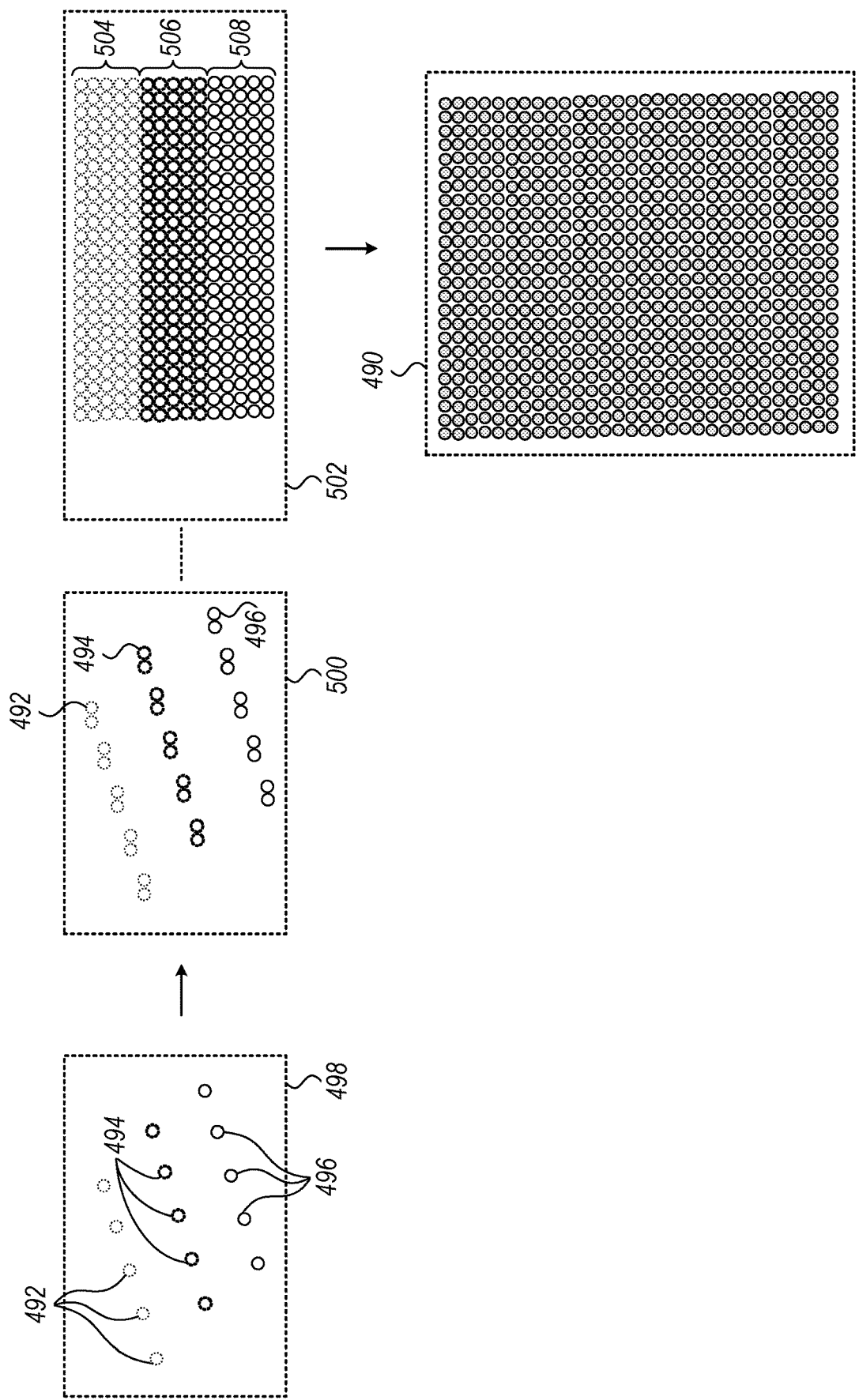
FIG. 29 is a schematic frontal view of a target irradiated by the optical sensing system of FIG. 28A over a sequence of scan times, in accordance with an embodiment of the invention.

FIG. 29 is a schematic frontal view of a target 490 irradiated by optical sensing system 480 over a sequence of scan times, in accordance with an embodiment of the invention. An initial frame 498 shows three tilted row of scan points 492, 494, 496, corresponding to the projections of the optical apertures of transducers 442 in the three parallel sensing devices 436 onto the target. As in the preceding embodiment, the tilt of the rows of scan points corresponds to the tilt between the row axes and the rotational axis of mirror 448. Frames 500, . . . , 502 show the scan points that are then acquired as scanner 446 sweeps the optical apertures horizontally across target 490. The three sets of scan points 492, 494, 496, covering corresponding horizontal bands 504, 506, 508, thus enable system 480 to scan the target rapidly with high resolution.

Additionally or alternatively, system 480 can be driven to scan each point on target 490 at multiple different wavelengths. For this purpose, each sensing device 436 operates at a different wavelength. Scanner 446 sweeps the optical apertures of transducers 442 in all the sensing devices so that each scan point 492, 494, 496 is scanned by a transducer at each of the different wavelengths at different points in the scan. The processor combines the signals from all the devices 436 to extract multi-wavelength data at each point.

Although the embodiments described above are directed specifically to reducing the scan pitch of optical transceiver cells, the principles of these embodiments may similarly be applied, mutatis mutandis, to other sorts of scanned arrays. For example, sensing cells 440 may comprise receiver cells, without transmission capabilities. Alternatively, sensing cells 440 may be replaced by emitters (such as red, green, and blue VCSELs, edge emitters, or micro-LEDs), and the scanning arrangements shown in the preceding figures may be applied in projecting patterns or images with fine resolution.

Boresighting of Multiple Optical Cells

The embodiment of FIG. 26A is useful in aligning multiple optical cells, such as sensing cells or optical transmitter cells along a common optical axis; but it requires that each of the cells or transmitters be disposed on a different substrate, with the substrates mounted on different sides of the beamsplitter cube. Alternatively, it is possible to align the axes of multiple cells that are mounted side by side on the same substrate, using a suitable arrangement of mirrors and beamsplitters mounted above the substrate, for example. Arrangements of this sort can be problematic, however, when the same focusing element, such as a collimation or projection lens, is to serve all the optical cells: If the optical path lengths from all the cells to the focusing element are not equal, the focusing element will project the optical apertures of the optical cells onto respective fields of view having different, respective angular sizes.

The embodiments of the present invention that are described in this section address this problem using path equalizers, i.e., optical or mechanical elements that adjust the effective focal lengths between the focusing element and the respective optical apertures of an array of optical cells. The term "effective focal length" means the distance from the focusing element to its back focal plane, taking into account both the geometrical length of each segment of the optical path and the refractive index of the medium through which the light propagates over the segment.

Thus, in the present embodiments, an array of reflectors are disposed along the optical axis of the focusing element at different, respective distances from the focusing element. Each reflector is positioned and configured to deflect radiation propagating between a respective one of the optical apertures of the optical cells and the focusing element. The path equalizers adjust the respective optical path length between each of the optical apertures and the focusing element so that all the effective focal lengths are equal (to within the required optical and mechanical tolerance). Consequently, the focusing element will apply the same focusing or collimation properties to all the optical apertures, as though they were physically collocated at the same point. Although the embodiments shown in the figures that follow illustrate the application of this sort of focal length equalization to arrays of three optical cells, the principles of these embodiments may alternatively be applied to arrays of two optical cells or to arrays of four or more optical cells.

Figure 30:
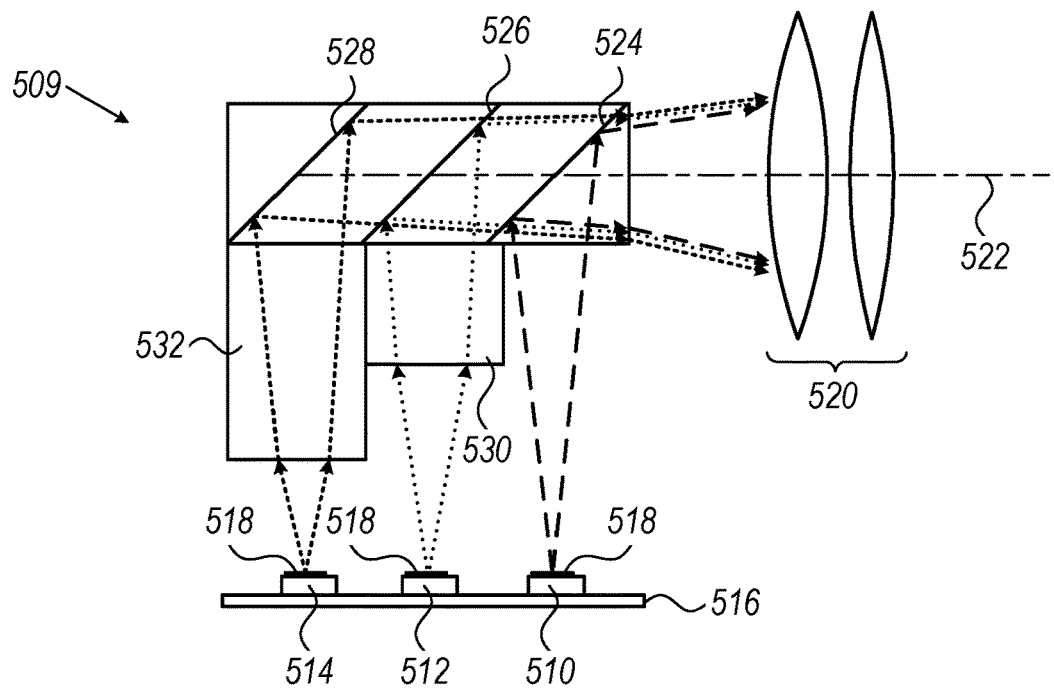
FIGS. 30 and 31 are schematic side views of optical systems including arrays of optical cells, in accordance with embodiments of the invention.

FIG. 30 is a schematic side views of an optical system 509 including an array of optical cells 510, 512, 514, in accordance with an embodiment of the invention. Optical cells 510, 512, 514 are mounted on a substrate 516 and have respective optical apertures 518. A focusing element 520, such as a lens, projects optical apertures 518 onto a target along an optical axis 522. An array of reflectors 524, 526, 528 are disposed along optical axis 522 so as to deflect radiation between cells 510, 512, 514, respectively, and focusing element 520. Typically, reflectors 524 and 526 are partial reflectors, while reflector 528, which is farthest from focusing element 520, is fully reflective. For example, assuming each of optical cells 510, 512, 514 transmits and/or receives optical radiation in a different, respective wavelength range, reflectors 524 and 526 may advantageously comprise dichroic reflectors with cutoff wavelengths between the wavelength ranges of the optical cells.

To compensate for the different physical lengths of the optical paths between cells 510, 512, 514 and focusing element 520, transparent dielectric blocks 530 and 532, of different, respective thicknesses, are introduced into the beam paths between optical cells 512, 514 and reflectors 526, 528, respectively. Blocks 530 and 532 serve as path equalizers. By principles of geometric optics, adding a dielectric material of thickness d and refractive index n between focusing element 520 and a given optical cell shifts the rear focal plane of the focusing element by a distance $\Delta f = d(1-1/n)$. Based on this principle, the thicknesses of blocks 530 and 532 are chosen so that optical apertures 518 of all of cells 510, 512, 514 are located at the rear focal plane, as illustrated in FIG. 30.

Figure 31:
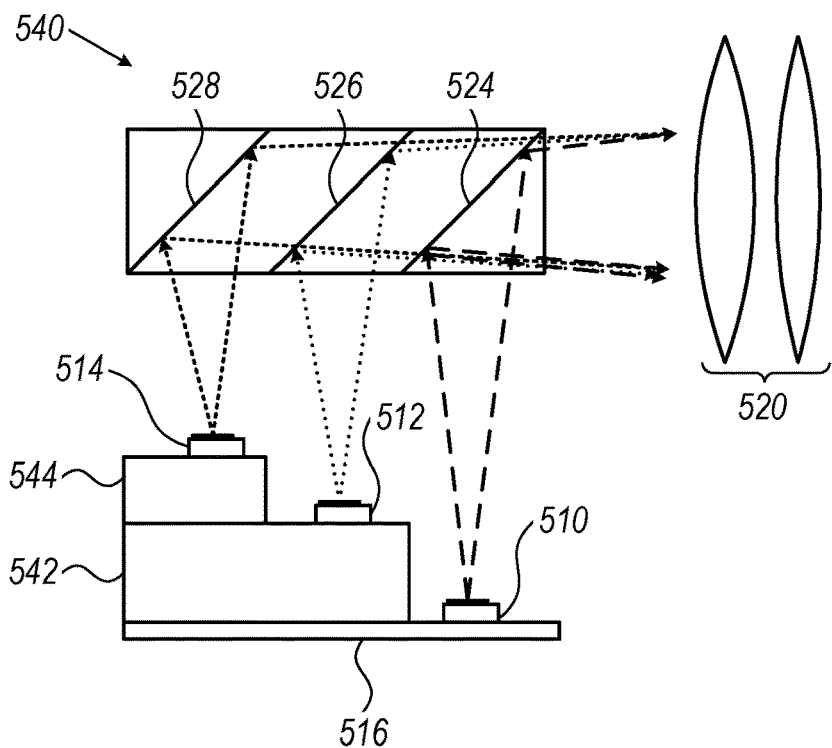

FIG. 31 is a schematic side views of an optical cells 510, 512, 514, in accordance with another embodiment of the invention. The arrangement of optical cells 510, 512, 514 and the corresponding reflectors 524, 526, 528 relative to focusing element 520 is similar to that in system 510 (FIG. 30). In system 540, however, pedestals 542, 544 of different respective heights serve as the path equalizers. Optical cells 512 and 514 are mounted on pedestals 542 and 544 respectively, thus shortening the total optical paths to focusing element 520, so that all the optical cells are located at the rear focal plane. If the mechanical tolerances of pedestals 542 and 544 are not tight enough to achieve the required optical precision, optical cells 512 and 514 can be positioned using active or vision-based alignment.

System Control and Scanning Over Regions of Interest

The description up to this point has focused on optical and photonic elements in systems and devices for optical sensing. These optical and photonic elements are supported by electronic control and processing circuits, as will now be described. In terms of electronic components, each sensing cell in the arrays described above typically comprises an analog front end, such as AFE circuit 126 (FIG. 4), and possibly other processing circuits, as well. The electronic components in the sensing cells are typically connected to convey output signals to central processing circuits, such as processor 48, by electrical buses 42 (FIG. 1). In some embodiments, the electronic functions of the sensing cells and central processing circuitry are switched and multiplexed in order to conserve electrical power and chip real estate, as well as to concentrate the processing resources of the system in regions of interest.

Figure 32:
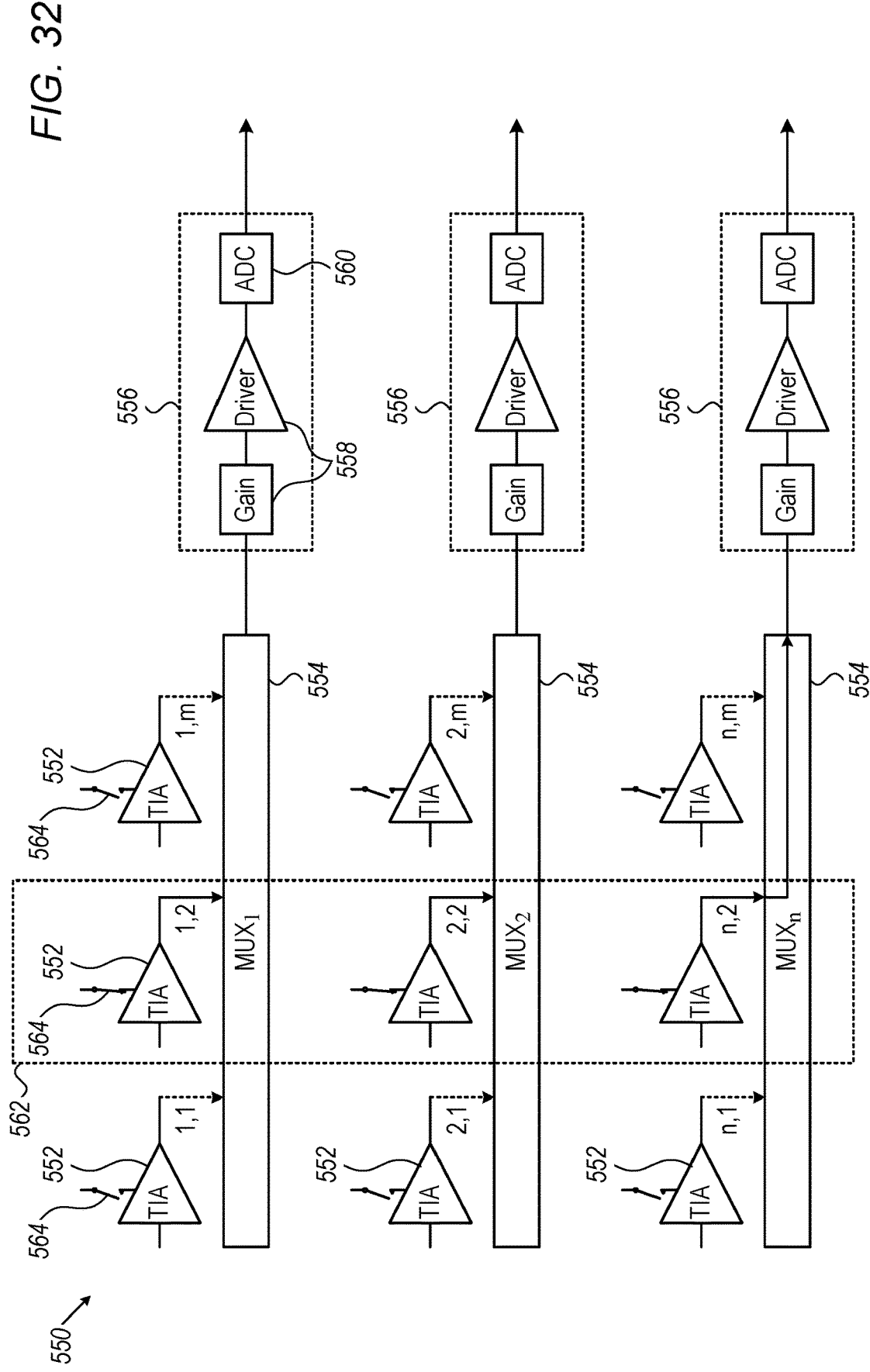
FIG. 32 is a block diagram that schematically illustrates signal processing circuits in an optical sensing system, in accordance with an embodiment of the invention.

FIG. 32 is a block diagram that schematically illustrates signal processing circuits 550 in an optical sensing system, in accordance with an embodiment of the invention. These circuits may be used, for example, in conjunction with the optical components of system 20 (FIG. 1), as well as with the other sensing cells and devices shown and described above.

Circuits 550 are assumed to be connected to a two-dimensional m×n array of sensing cells. Each sensing cell comprises a respective transimpedance amplifier (TIA) 552 as its analog front end. Each row of the array is connected to a respective multiplex bus 554, which is in turn connected to a readout circuit 556 comprising analog processing circuits 558 and an analog/digital converter (ADC) 560. Each TIA 552 can be switched on or off by a respective switch 564. Thus a given column 562 of the array of sensing cells is switched on by closing respective switches 564, while the remaining columns are switched off by opening the switches. Alternatively, TIAs 552 can be switched on and off individually, not necessarily by column.

The signals from the sensing cells in column 562 are conveyed via buses 554 to readout circuits 556, which pass digital output values to processor 48 (FIG. 1). Columns 562 may be activated in this manner sequentially. Alternatively, only the columns in a certain region of interest may be turned on, while the remaining columns remain dormant Processor 48 may also control the integration times of the sensing cells by setting the lengths of time over which switches 564 are closed. Longer integration times may be used, for example, to enhance the signal/noise ratio (SNR) of measurements made in regions of interest and/or regions giving weak signals, such as in distant areas in a LIDAR map.

Figure 33:
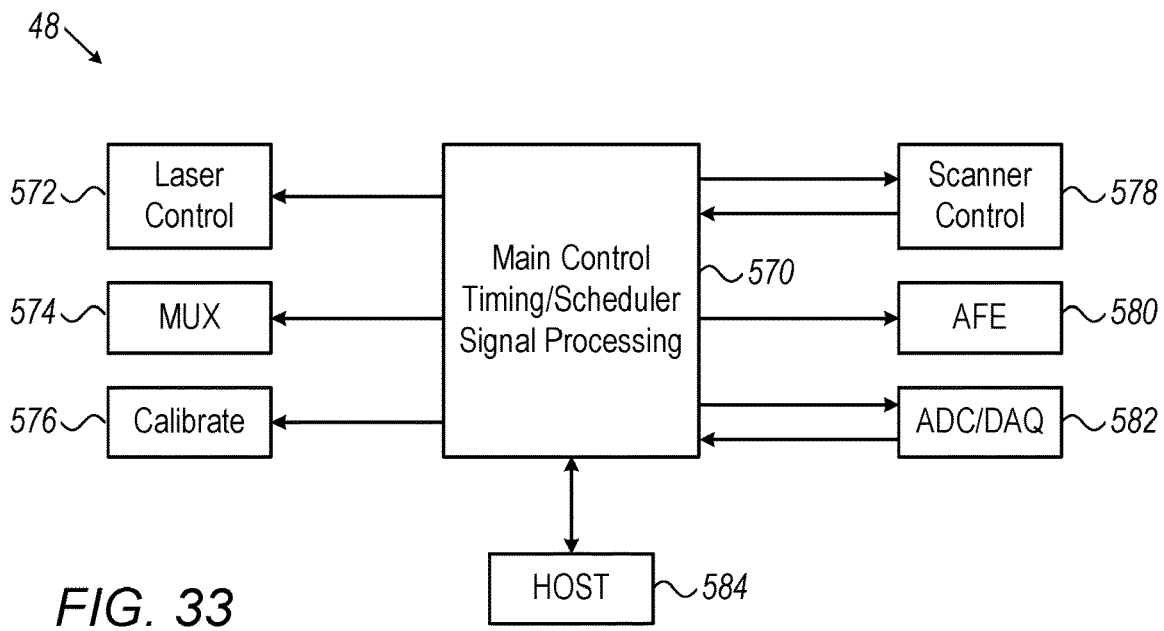
FIG. 33 is a block diagram that schematically illustrates electronic circuit components associated with an optical sensing system, in accordance with an embodiment of the invention.

FIG. 33 is a block diagram that schematically illustrates electronic circuit components associated with processor 48 in an optical sensing system, such as system 20 (FIG. 1), in accordance with an embodiment of the invention. As noted earlier, some of these functions are typically carried out in software or firmware by a programmable processor, such as a microprocessor or microcontroller. Other functions may be carried by digital logic, along with digital and analog processing and interface circuits.

A main controller 570, in conjunction with a host processor 584, controls and coordinates the functions of the system, including allocation of system resources depending on identified regions of interest and sensing tasks. Thus, for example, main controller 570 drives a laser controller 572, which sets the power and modulation profile of the laser light that is supplied to the sensing cells and transmitted toward the target. Additionally or alternatively, laser controller 572 may scan the laser wavelength over a selected range or in a random-access fashion, in accordance with application requirements. Main controller 570 concurrently drives a scanner controller 578, which controls the speed at which the optical apertures of the sensing cells are scanned over the target and the range of the scan. In addition, main controller 570 drives multiplexing circuits 574, which select the sensing cells to activate at any given point in the scan. For example, multiplexing circuits 574 may switch electronic components, such as TIAs 552 (FIG. 32), on and off, as well as controlling the distribution of coherent radiation to the sensing cells, by means such as switch networks 68 and 76 (FIG. 2).

The above switching and selection functionalities enable the system to focus its detection and processing resources in particular regions of interest, as described further hereinbelow. Main controller 570 receives feedback from scanner controller 578 with respect to the actual scanner position at any instant, so that the signals received from the sensing cells can be associated with the correct coordinates in a map of the target produced by controller 570.

For accurate sensing, main controller 570 also interacts with calibration functions 576 and controls settings of analog front end (AFE) circuits 580. The calibration functions include clock synchronization, timing, and power monitoring. APE settings include functions such as amplifier gain control and filtering. In addition, main controller 570 sets sampling clocks and parameters for analog/digital conversion (ADC) and digital data acquisition (DAQ) circuits 588. Main controller 570 receives and processes digital data from circuits 588 in order to extract information regarding the range, shape and velocity of the target.

In some embodiments of the present invention, these processing and control capabilities are used in scanning the target selectively, to identify and extract detailed information with respect to regions of interest. These embodiments use an array of transceiver cells, which have respective optical apertures, defining respective fields of view, as described above. These transceiver cells, when activated by main controller 570, transmit respective beams of coherent radiation toward a target and receive the coherent radiation reflected from the target through the respective optical apertures.

To make optimal use of the available sensing and processing resources, the fields of view of the transceiver cells are first scanned across a target area at a certain (typically coarse) resolution, and the signals output by the transceiver cells are processed to identify a region of interest within the target area. For example, processor 48 may identify shapes and ranges of objects in this first scan and select a region or regions contain objects of interest.

After identifying a region of interest in this manner, the fields of view of the transceiver cells are scanned selectively across the region of interest, typically with a resolution finer than the resolution of the first scan. The signals output by the transceiver cells during the high-resolution scan are processed in order to produce a high-quality three-dimensional (3D) map of the region of interest. Specific techniques for selecting and scanning the region of interest and enhancing the quality of 3D mapping in the region are described with reference to the figures that follow.

Figure 34:
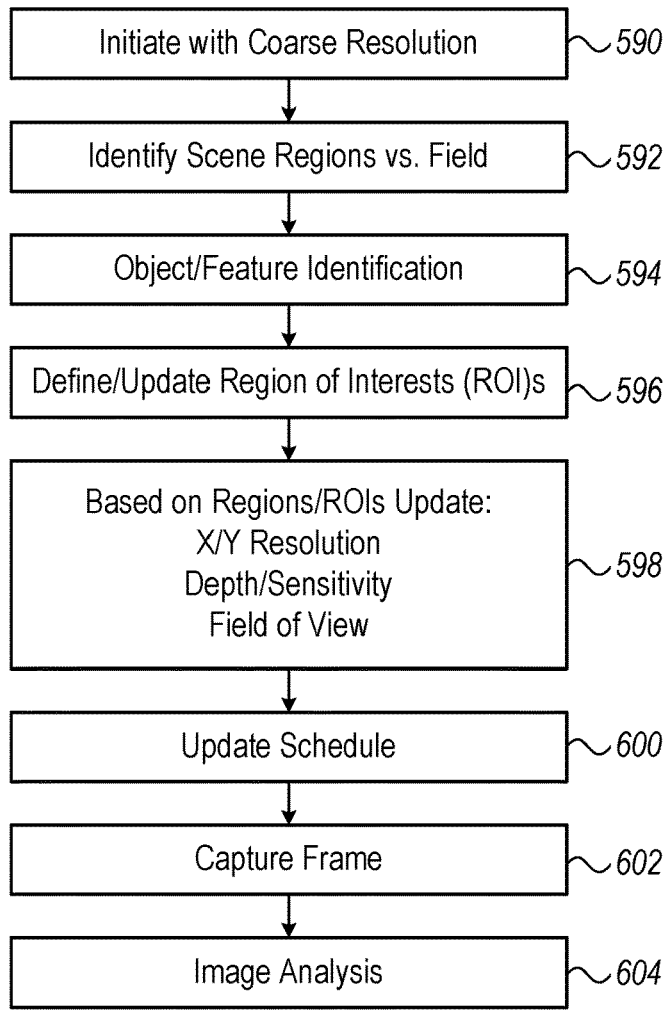
FIG. 34 is a flow chart that schematically illustrates a method for selective scanning of an optical sensing system, in accordance with an embodiment of the invention.

FIG. 34 is a flow chart that schematically illustrates a method for selective scanning of an optical sensing system, in accordance with an embodiment of the invention. For the sake of convenience and clarity, this method will be described with reference to the elements of system 20 (FIG. 1). Alternatively, aspects of this method may be implemented using features described hereinabove with reference to other figures, as well as using other sorts of scanned coherent sensing arrays with suitable capabilities.

System 20 performs an initial scan of a target area with coarse resolution, at an initial scanning step 590. Typically, in this step, scanner 46 scans across the entire target area at a high scanning speed and/or allocates a short integration time to signal collection at each point in the scan. (The "high" scanning speed and "short" integration time are relative to the values of scanning speed and integration time that will be applied in subsequent scans.) Additionally or alternatively, processor 48 sets the optical and electronic multiplexing circuits in system 20 so that only a subset of sensing cells 34 transmit coherent radiation and receive and output signals to the processor. Thus, the depth map generated at step 590 will cover a large angular range with coarse resolution and low signal/noise ratio (SNR) relative to subsequent scans.

Processor 48 analyzes the depth map created at step 590 to segment the field of view of the scan into regions, at a region identification step 592. The regions may be characterized, for example, by particular ranges of depth or detail. Processor 48 selects the regions that meet criteria appropriate to the mapping task, for example regions at a certain range or containing particular sorts of detail. The processor segments the depth map within the selected regions to identify and label objects and features in the selected regions, at an object identification step 594. For example, in a LIDAR application, the processor may identify shapes that appear to be people or vehicles; or in an OCT application, the processor may identify certain anatomical features.

Based on the locations and depths of the regions identified in step 592 and the objects and features identified in step 594, processor 48 defines one or more regions of interest for high-resolution scanning, at an ROI definition step 596. In this step, the processor defines both the lateral boundaries of the regions of interest and the respective depths.

For each ROI, processor 48 sets scan parameters that will be applied in a subsequent scan over each ROI, at a parameter update step 598. The parameters may include:

Scan speed—Typically (although not necessarily), the ROIs will be scanned at a slower speed than in the initial scan, in order to achieve finer resolution and better SNR. The scan speed over each ROI may also depend on the depth of the ROI. Specifically, more distant ROIs may be scanned at a lower angular scanning rate than short-range ROIs in order to reduce the loss of spatial resolution with distance.

Transverse resolution—As noted earlier, during the initial scan at step 590, processor 48 may activate only a subset of sensing cells 34. At step 598, processor 48 may decide to activate a larger set of the sensing cells, typically a superset of the sensing cells that were activated in the initial scan, in scanning over an ROI.

As a result, the ROI will be scanned with higher scan density, and thus higher resolution.

Transmitted radiation intensity—Particularly for distant regions of interest, processor 48 may set the intensity of the transmitted coherent radiation to a higher value. The increased intensity will enhance the amplitude of the signals received by sensing cells 34 and thus improve the SNR. Alternatively, for nearby regions of interest, the intensity may be reduced. The intensity of transmission from a given sensing cell can be adjusted, for example, by switching the coherent radiation from the laser to the bus serving the cell, as well as selecting the number of cells among which the radiation is to be divided.

Integration time—As noted earlier, the integration times of sensing cells 34 can be increased by extending the periods of time over which the cells receive and transmit coherent radiation from the laser, as well as extending the periods over which the cells are actively multiplexed to the readout circuits. Thus, during the scans over regions of interest, the integration time may be set to a greater value than during the initial scan. Additionally or alternatively, the amplifier gain applied by the AFE can be increased or decreased as appropriate.

Based on the scan parameter settings determined at step 598, processor 48 sets the schedule for the subsequent scan or scans, at a schedule update step 600. The schedule specifies the geometrical boundaries of the scan windows and the allocation of system resources within each window, such as scan speed, resolution, and distribution of coherent radiation intensity among sensing cells 34. Processor 48 then drives system 20 to scan a subsequent frame with the updated scan parameters, at a scan capture step 602. Processor 48 applies image analysis algorithms to the depth map resulting from the second frame in order to identify objects of interest, at an analysis step 604. The analysis results may be used as input in repeating steps 596 and 598, to update the scan parameters for a subsequent scan.

Figure 35:
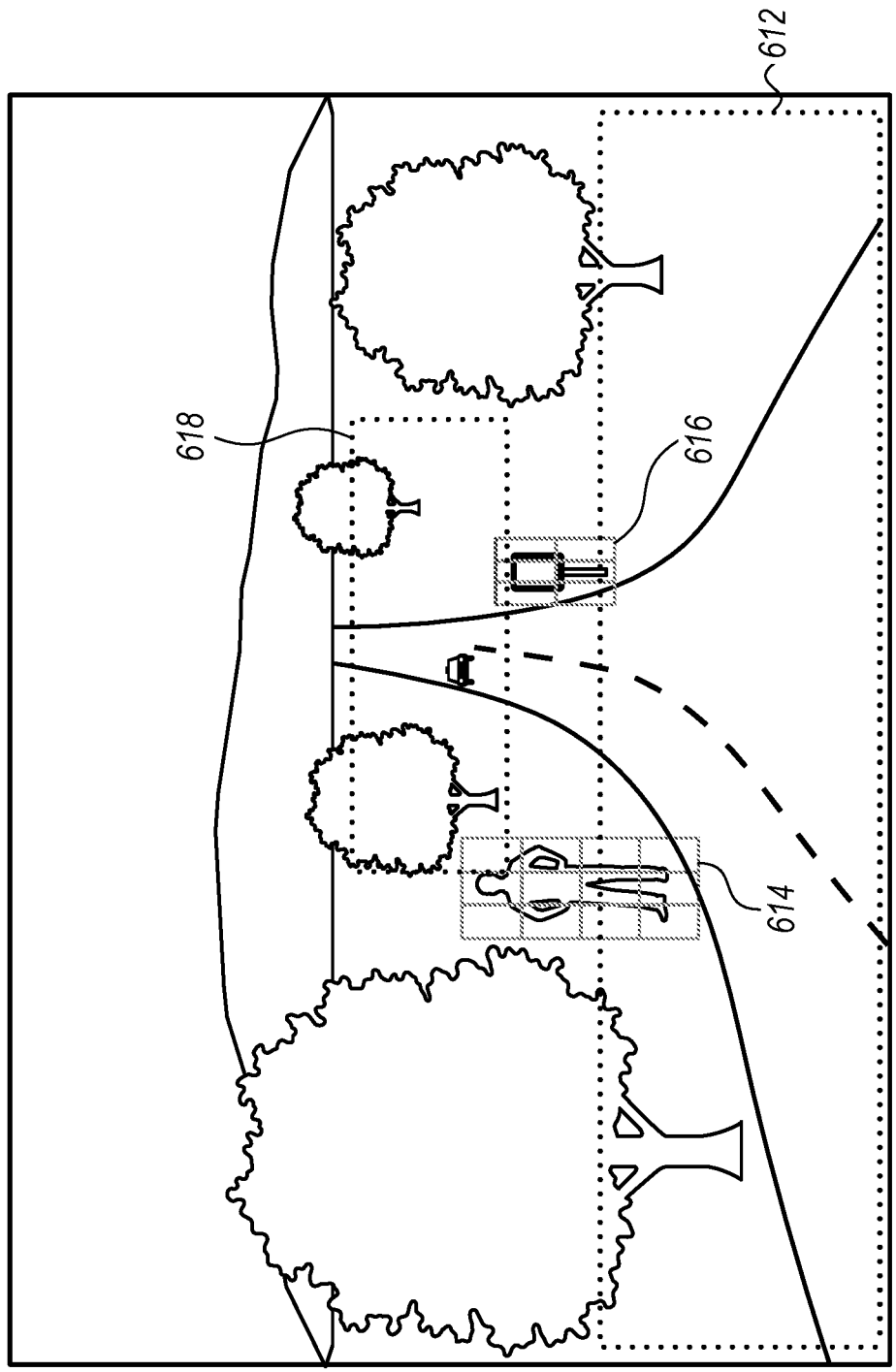
FIG. 35 is a schematic frontal view of a scene that is scanned by an optical sensing system, in accordance with an embodiment of the invention.

FIG. 35 is a schematic frontal view of a scene 610 that is scanned by an optical sensing system, such as system 20 (FIG. 1), in accordance with an embodiment of the invention. System 20 scans scene 610 with coarse resolution at step 590, and thus identifies regions and features of the scene at steps 592 and 594. In the present example, these regions include:

A short-range region 612. In the absence of objects of interest within this region, processor 48 will set a low scan resolution for this region in step 598.

Regions of interest 614, 616. Processor 48 recognizes that these mid-range regions contain objects of possible significance. Therefore, processor 48 will set a high scan resolution and low scan speed for these regions in step 598.

A long-range region of interest 618. Processor 48 recognizes that this region contains objects of importance, including the road and other vehicles, at large distances from the sensing system. Therefore, at step 598, processor 48 will assign a reduced scan speed and increased transmitted radiation intensity for scanning this region.

Figure 36:
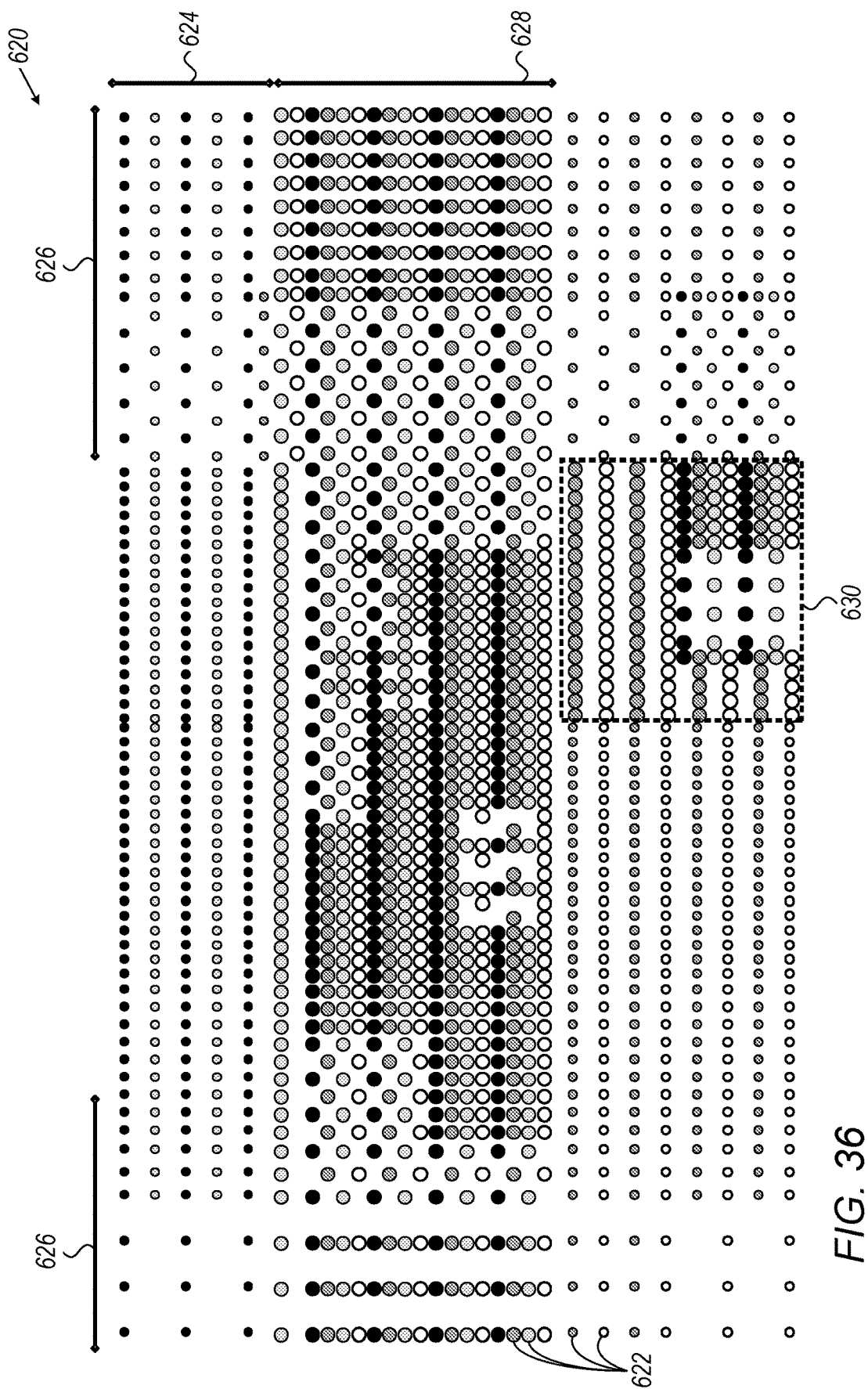
FIG. 36 is a schematic frontal view of a scan pattern applied across a scene by an optical sensing system, in accordance with an embodiment of the invention.

FIG. 36 is a schematic frontal view of a scan pattern 620 applied across a scene by an optical sensing system, in accordance with an embodiment of the invention. This figure corresponds to the frame captured at step 602 (FIG. 34), using the schedule set at step 600. Each spot 622 in scan pattern 620 marks a scan point acquired by the system, while the size of the spot represents the transmitted intensity or integration time at the point.

FIG. 36 illustrates the use of preferential switching and application of optical power in the areas of a scene, such as scene 610, that are considered to contain information of value, while reducing resource use in less interesting areas. Thus, the upper part of scan pattern 620 corresponds to a short-range area 624 of the scene, which is scanned at coarse resolution. Peripheral parts 626 of this short-range area are scanned at higher speed, for example by increasing the rate of movement of scanner 46 (FIG. 1). A longer-range region 628 containing features of interest is scanned with higher scan density, integration time, and transmitted power. The scan density, integration time, and transmitted power are likewise increased within the bounds of a local region of interest 630. The regions of interest in the scene are defined and scanned adaptively using the interplay between switching, multiplexing, integration time, transmit power, and scanning speed, as explained above.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An optoelectronic device, comprising:
 a planar substrate;
 an optical bus comprising at least one waveguide disposed on the substrate and configured to convey coherent radiation through the bus; and
 an array of sensing cells disposed on the substrate along the optical bus, each sensing cell comprising:
  at least one tap coupled to extract a portion of the coherent radiation propagating through the optical bus;
  an optical transducer, configured to couple optical radiation between the sensing cell and a target external to the substrate; and
  a receiver, which is coupled to mix the coherent radiation extracted by the tap with the optical radiation received by the optical transducer and to output an electrical signal responsively to the mixed radiation.

2. The device according to claim 1, wherein the optical bus comprises multiple buses serving different, respective sets of the sensing cells, and wherein the device comprises an optical network coupled to distribute the coherent radiation from a radiation source to the multiple buses.

3. The device according to claim 2, wherein the optical network comprises an active switch network.

4. The device according to claim 2, wherein the optical network comprises a passive splitter array.

5. The device according to claim 1, wherein the sensing cells have respective fields of view, which are defined by respective optical apertures of the optical transducers, and wherein the device comprises a scanner, which is configured to scan the fields of view over the target.

6. The device according to claim 5, wherein the optical apertures are disposed in a row, which has a row axis perpendicular to a scan direction of the scanner.

7. The device according to claim 5, wherein the optical apertures of the sensing cells are located at respective nodes on respective rows and columns of a two-dimensional rectangular grid such that only a minority of the nodes on the respective rows and columns are occupied by the optical transducers, and
> wherein the scanner is configured to scan the optical apertures across the target along at least the rows of the grid so that each of the optical apertures is projected successively onto a respective sequence of multiple nodes in the rectangular grid on the target.

8. The device according to claim 1, wherein each sensing cell comprises:
  a transmit waveguide, which is configured to convey the coherent radiation from the at least one tap to the optical transducer for transmission toward the target; and
  a receive waveguide, which is configured to convey the optical radiation received by the optical transducer to the receiver.

9. The device according to claim 8, wherein the at least one tap comprises a first tap coupled to convey a first part of the coherent radiation from the bus to the transmit waveguide and a second tap coupled to convey a second part of the coherent radiation to the receiver for mixing with the received optical radiation.

10. The device according to claim 9, wherein the optical bus comprises a single waveguide to which both the first and second taps are coupled.

11. The device according to claim 9, wherein the optical bus comprises a first waveguide, to which the first tap is coupled, and a second waveguide, to which the second tap is coupled.

12. The device according to claim 8, wherein in each cell, the optical transducer comprises a first transducer element configured to couple the coherent radiation out of the transmit waveguide toward the target and a second transducer element configured to couple the optical radiation that is incident on the optical transducer into the receive waveguide.

13. The device according to claim 8, wherein each cell comprises a coupler configured to couple the coherent radiation from the transmit waveguide to the optical transducer for transmission toward the target and to couple the optical radiation that is incident on the optical transducer into the receive waveguide.

14. The device according to claim 13, wherein the coherent radiation conveyed by the transmit waveguide has a first polarization, and
> wherein the optical transducer is configured to receive and convey to the coupler the incident optical radiation of both the first polarization and a second polarization, orthogonal to the first polarization, and the coupler is configured to couple the optical radiation received with both the first and second polarizations to the receiver.

15. The device according to claim 14, wherein the coupler comprises a polarization beamsplitter rotator, which is configured to rotate the received optical radiation with the second polarization to the first polarization.

16. The device according to claim 15, wherein the optical transducer comprises an edge coupler, and the polarization beamsplitter rotator is integrated with the edge coupler.

17. The device according to claim 8, wherein the optical transducer comprises a grating coupler, which comprises a first grating coupled to the transmit waveguide and a second grating coupled to the receive waveguide.

18. The device according to claim 17, wherein the first grating is configured to couple the coherent radiation between the transmit waveguide and a first range of angles in a space over the substrate, and the second grating is configured to couple the optical radiation that is incident on the grating coupler within a second range of angles, different from the first range, into the receive waveguide.

19. The device according to claim 1, wherein the optical transducer is configured to receive and convey to the receiver the incident optical radiation of both a first polarization and a second polarization, orthogonal to the first polarization, and
> wherein the receiver comprises a first mixer and a first detector for mixing and detecting the received optical radiation of the first polarization and a second mixer and a second detector for mixing and detecting the received optical radiation of the second polarization.

20. The device according to claim 1, wherein the optical transducer comprises an edge coupler.

21. The device according to any f claim 1, wherein the optical transducer comprises a grating coupler.

22. The device according to any f claim 1, wherein the signal output by the receiver in each sensing cell comprises a beat frequency responsive to a range of the target from the device.

23. The device according to claim 22, wherein the receiver in each sensing cell comprises an optical hybrid and a pair of detectors, which are coupled to receive in-phase (I) and quadrature (Q) components of the mixed radiation and to output corresponding I and Q components of the electrical signal.

24. A method for sensing, comprising:
  conveying coherent radiation through an optical bus comprising at least one waveguide disposed on a substrate;
  providing an array of sensing cells disposed on the substrate along the optical bus, each sensing cell comprising at least one tap coupled to extract a portion of the coherent radiation propagating through the optical bus;
  coupling optical radiation between each sensing cell and a target external to the substrate via an optical transducer associated with the sensing cell;
  mixing the coherent radiation extracted by the tap in each sensing cell with the optical radiation received by the optical transducer; and
  outputting an electrical signal from each of at least some of the sensing cells responsively to the mixed radiation.

25. The method according to claim 24, wherein the optical bus comprises multiple buses serving different, respective sets of the sensing cells, and wherein the method comprises distributing the coherent radiation from a radiation source to the multiple buses via an optical network.

26. The method according to claim 25, wherein the optical network comprises an active switch network.

27. The method according to claim 25, wherein the optical network comprises a passive splitter array.

28. The method according to claim 24, wherein the sensing cells have respective fields of view, which are defined by respective optical apertures of the optical transducers, and wherein the method comprises scanning the fields of view over a target.

29. The method according to claim 28, wherein the optical apertures are disposed in a row, which has a row axis, and wherein scanning the fields of view comprises scanning in a scan direction perpendicular to the row axis.

30. The method according to claim 28, wherein the optical apertures of the sensing cells are located at respective nodes on respective rows and columns of a two-dimensional rectangular grid such that only a minority of the nodes on the respective rows and columns are occupied by the optical transducers, and wherein scanning the fields of view comprises scanning the optical apertures across the target along at least the rows of the grid so that each of the optical apertures is projected successively onto a respective sequence of multiple nodes in the rectangular grid on the target.

31. The method according to claim 24, wherein each sensing cell comprises:
   a transmit waveguide, which is configured to convey the coherent radiation from the at least one tap to the optical transducer for transmission toward the target; and
   a receive waveguide, which is configured to convey the optical radiation received by the optical transducer to the receiver.

32. The method according to claim 31, wherein the at least one tap comprises a first tap coupled to convey a first part of the coherent radiation from the bus to the transmit waveguide and a second tap coupled to convey a second part of the coherent radiation to the receiver for mixing with the received optical radiation.

33. The method according to claim 32, wherein the optical bus comprises a single waveguide to which both the first and second taps are coupled.

34. The method according to claim 32, wherein the optical bus comprises a first waveguide, to which the first tap is coupled, and a second waveguide, to which the second tap is coupled.

35. The method according to claim 31, wherein each optical transducer comprises a first transducer element configured to couple the coherent radiation out of the transmit waveguide toward the target and a second transducer element configured to couple the optical radiation that is incident on the optical transducer into the receive waveguide.

36. The method according to claim 31, wherein coupling the optical radiation comprises coupling the coherent radiation from the transmit waveguide to the optical transducer for transmission toward the target and coupling the optical radiation that is incident on the optical transducer into the receive waveguide.

37. The method according to claim 36, wherein the coherent radiation conveyed by the transmit waveguide has a first polarization, and
   wherein coupling the optical radiation that is incident on the optical transducer comprises receiving via the optical transducer the incident optical radiation of both the first polarization and a second polarization, orthogonal to the first polarization, and coupling the optical radiation received with both the first and second polarizations to a receiver, which outputs the electrical signal.

38. The method according to claim 37, wherein receiving the incident optical radiation of both the first polarization and the second polarization comprises coupling the received optical radiation into a polarization beamsplitter rotator, which rotates the received optical radiation with the second polarization to the first polarization.

39. The method according to claim 38, wherein the optical transducer comprises an edge coupler, and the polarization beamsplitter rotator is integrated with the edge coupler.

40. The method according to claim 31, wherein the optical transducer comprises a grating coupler, which comprises a first grating coupled to the transmit waveguide and a second grating coupled to the receive waveguide.

41. The method according to claim 40, wherein coupling the optical radiation comprise coupling the coherent radiation via the first grating between the transmit waveguide and a first range of angles in a space over the substrate, and coupling the optical radiation that is incident on the grating coupler within a second range of angles, different from the first range, via the second grating into the receive waveguide.

42. The method according to claim 24, wherein coupling the optical radiation comprises receiving and conveying to the receiver the incident optical radiation of both a first polarization and a second polarization, orthogonal to the first polarization, and
   wherein mixing the coherent radiation comprises mixing and detecting the received optical radiation of the first polarization in a first detector and mixing and detecting the received optical radiation of the second polarization in a second detector.

43. The method according to claim 24, wherein the optical transducer comprises an edge coupler.

44. The method according to claim 24, wherein the optical transducer comprises a grating coupler.

45. The method according to claim 24, wherein the electrical signal output by each sensing cell comprises a beat frequency responsive to a range of the target.

46. The method according to claim 45, wherein each sensing cell comprises an optical hybrid and a pair of detectors, which are coupled to receive in-phase (I) and quadrature (Q) components of the mixed radiation and to output corresponding I and Q components of the electrical signal.

\* \* \* \* \*